(12) United States Patent
Castor

(10) Patent No.: US 8,703,727 B2
(45) Date of Patent: Apr. 22, 2014

(54) NANOTECHNOLOGY FORMULATION OF POORLY SOLUBLE COMPOUNDS

(75) Inventor: Trevor Percival Castor, Arlington, MA (US)

(73) Assignee: Aphios Corporation, Woburn, MA (US)

( * ) Notice: Subject to any disclaimer, the term of this patent is extended or adjusted under 35 U.S.C. 154(b) by 0 days.

(21) Appl. No.: 13/216,125

(22) Filed: Aug. 23, 2011

(65) Prior Publication Data

US 2012/0052120 A1 Mar. 1, 2012

Related U.S. Application Data

(60) Provisional application No. 61/402,103, filed on Aug. 24, 2010.

(51) Int. Cl.
*A61K 9/14* (2006.01)

(52) U.S. Cl.
USPC .................................. 514/42; 424/490

(58) Field of Classification Search
None
See application file for complete search history.

(56) References Cited

U.S. PATENT DOCUMENTS

2007/0072939 A1* 3/2007 Kupper .......................... 514/454
2007/0154554 A1* 7/2007 Burgermeister et al. ..... 424/486

OTHER PUBLICATIONS

Wischke et al. Developement of PLGA based injectable delivery systems for hydrophobic fenretinide, Pharm Res, Oct. 27, 2010 (10): 2063-74, Epub Jul. 29, 2010.*
Shekunov et al., Engineering of composite particles for drug delivery using supercritical fluid technology, Polymeric Drug Delivery II, 2006.*
Holzer et al., Physico-Chemical characterization of PLGA nanoparticles after freese drying and storage, Eur. J. Pharm. Biopharm, 2009.*
Vandervoort et al., Biocompaticlble stabilixers in the preparation of PLGA nanoparticles, a factorial design study, Int't J. Pharm 238, 2002.*

* cited by examiner

*Primary Examiner* — Anand Desai
*Assistant Examiner* — Melissa Mercier
(74) *Attorney, Agent, or Firm* — Lathrop & Gage LLP; Anthony J. Janiuk

(57) ABSTRACT

Embodiments of the present invention are directed to articles of manufacture, spheres having a diameter of 50 to 500 nanometers which contain poorly soluble drugs and methods of making such spheres. Embodiments of the present invention have particular application for the following drug candidates and closely related poorly soluble derivatives of such candidates: (i) indole hydrazinecarbothioamide [NSC 73306]; (ii) fenretinide (4HPR) [NSC 374551]; (iii) safingol [NSC 714503]; (iv) 17-allylamino demethoxygeldanamycin (17-AAG) [NSC 330507]; and (v) an aminoflavone drug [NSC 686288].

10 Claims, 23 Drawing Sheets

Figure 4: SuperFluids™ Solubility (SOL) Apparatus

Figure 5: PLGA

Poly(D,L-lactide-co-glycolide) 50:50
$(C_3H_4O_2)_n(C_2H_2O_2)_m$
n : m = 1 : 1

Figure 6: Solubility of Resomer® RG 502 PLGA in SuperFluids™ 90 % CO2:10 % Ethanol at 45°C Figure 7a                    Figure 7b

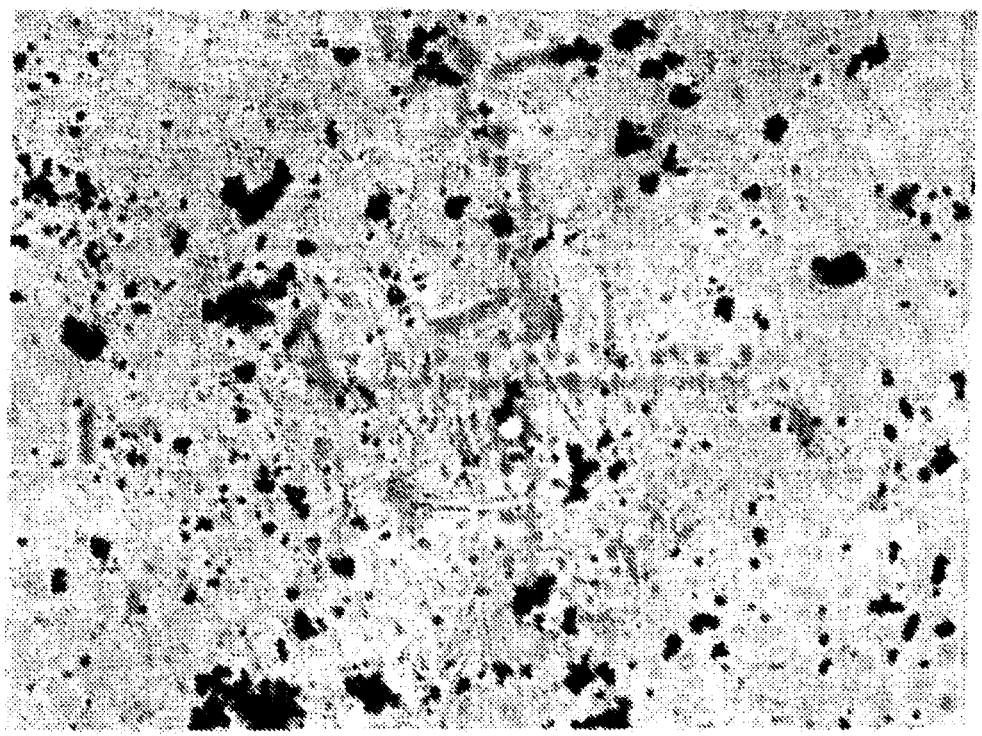
Figure 10: Photomicrograph of Aminoflavone Nanoparticles After SuperFluids™ Particle Size Reduction (BPN-16) at a Magnification of 400X

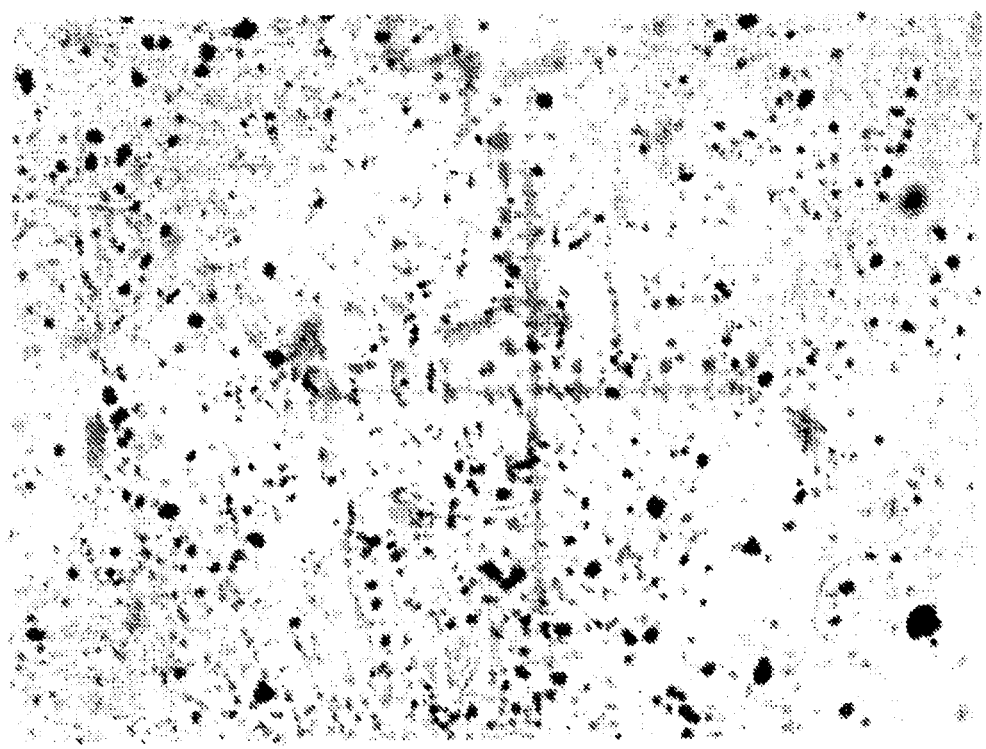
Figure 11: Photomicrograph of Aminoflavone Nanoparticles After SuperFluids™ Particle Size Reduction (BPN-17) at a Magnification of 200X

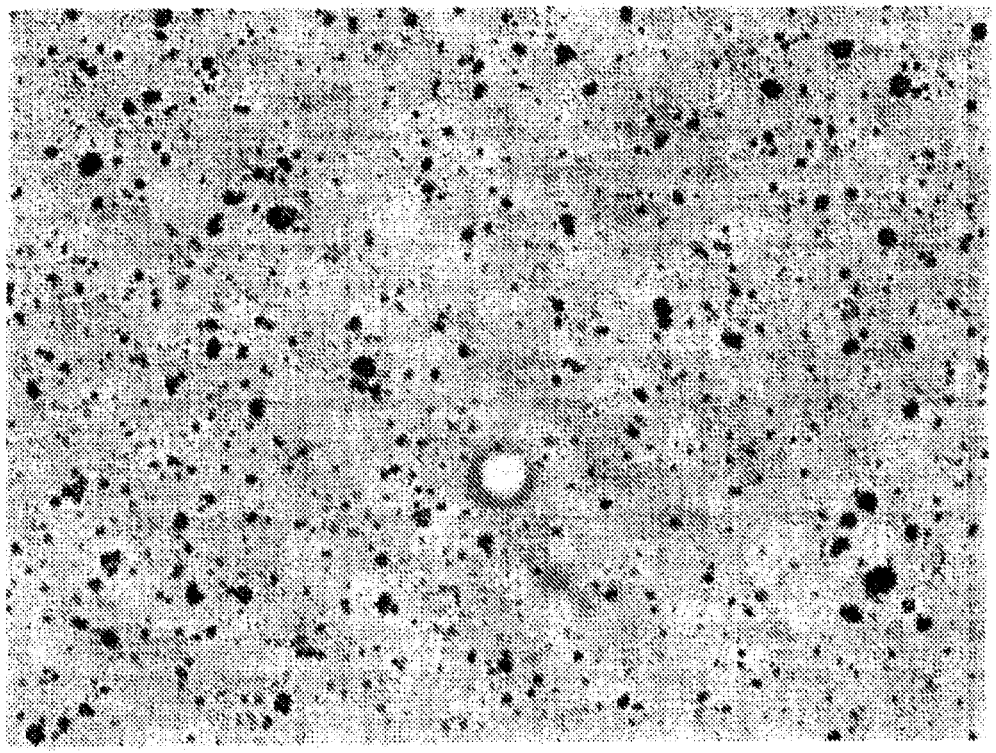
Figure 12: Photomicrograph of Aminoflavone Nanoparticles After SuperFluids™ Particle Size Reduction (BPN-19) at a Magnification of 200X Figures 13a and 13b: Photomicrographs of 17-AAG Particles Before and After SuperFluids™ Particle Size Reduction (BPN-21) at a Magnification of 200X Figure 14: Solubility of Aminoflavone in DI Water and 1% PVA
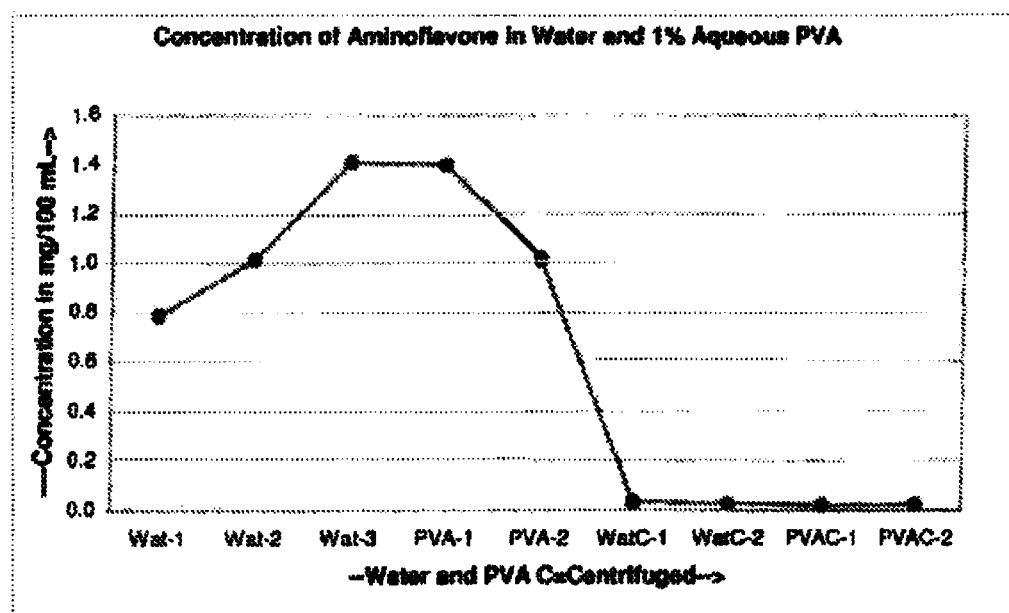

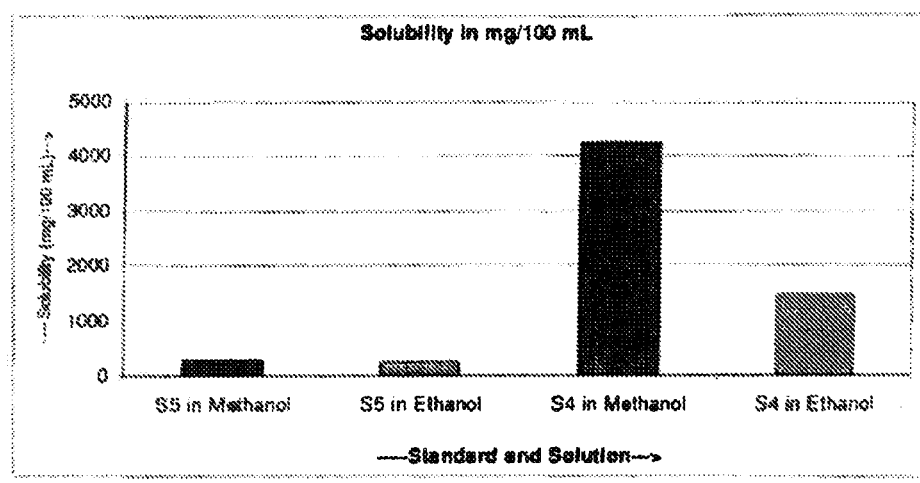
Figure 15: Solubilities of Aminoflavone and 17-AAG in Methanol and Ethanol at 25° C

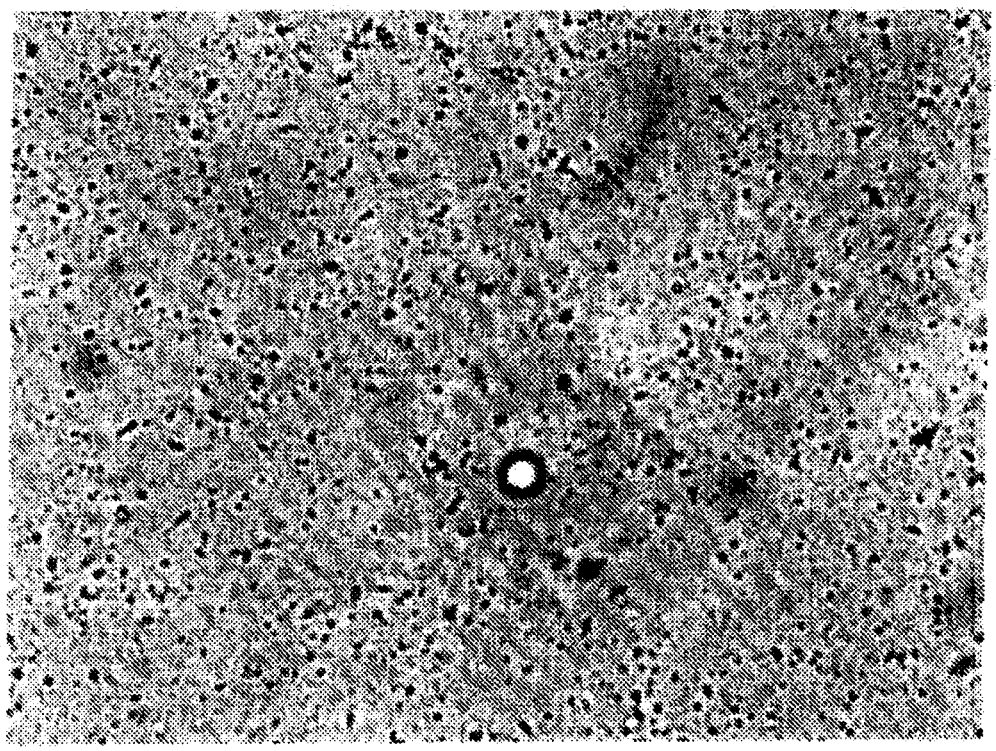
Figure 18: Photomicrograph of BPN-13 Polymer Nanospheres Product

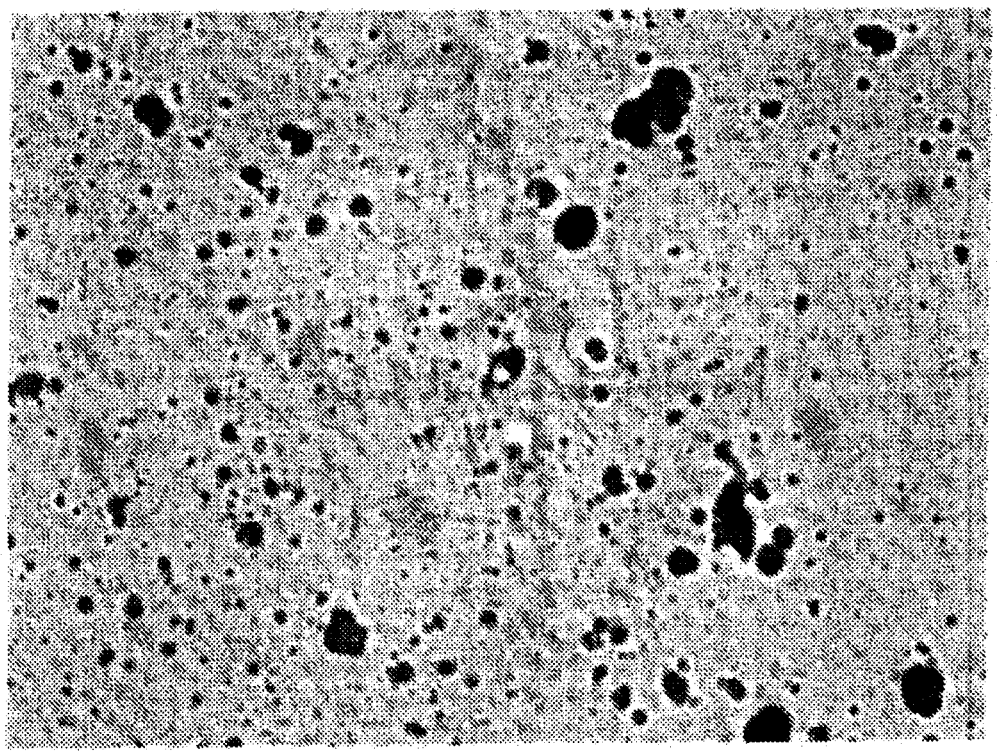
Figure 19: Photomicrograph of BPN-14 Polymer Nanospheres Product (400X)

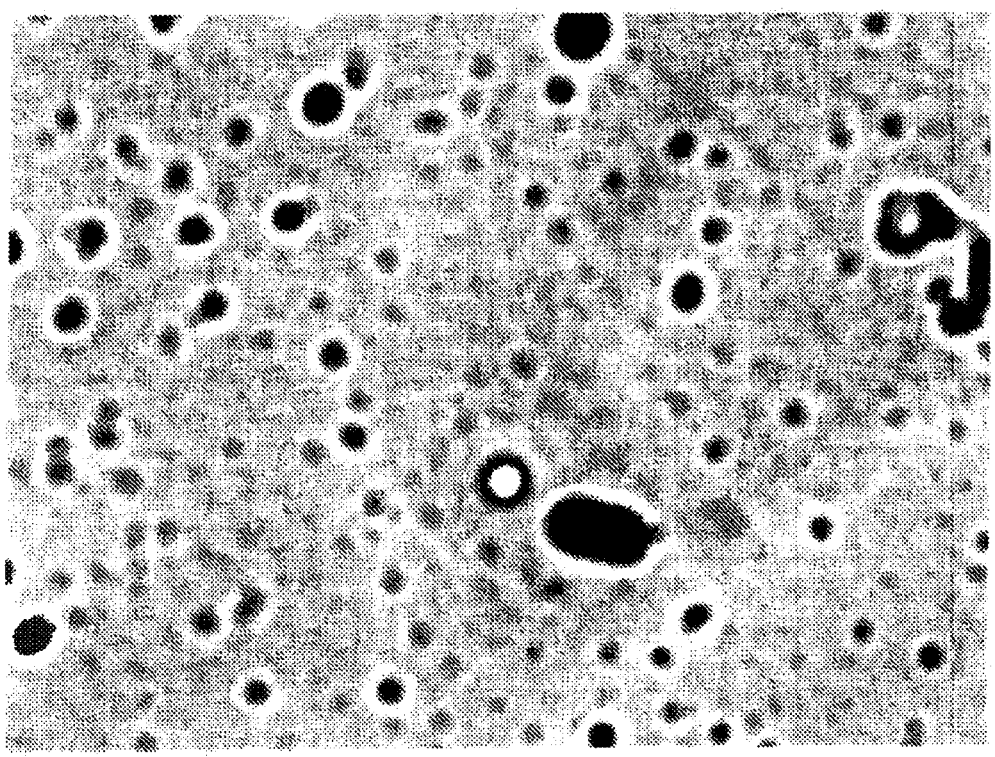
Figure 20: Photomicrograph of BPN-18 Polymer Nanospheres Product (400X)

Figures 21a and 21b: Photomicrograph of BPN-20 Nanospheres Product (A) and Supernatant (B)

Figures 22a and 22b: Photomicrographs of BPN-23 Polymer Nanospheres Product (A) and Overflow (B)

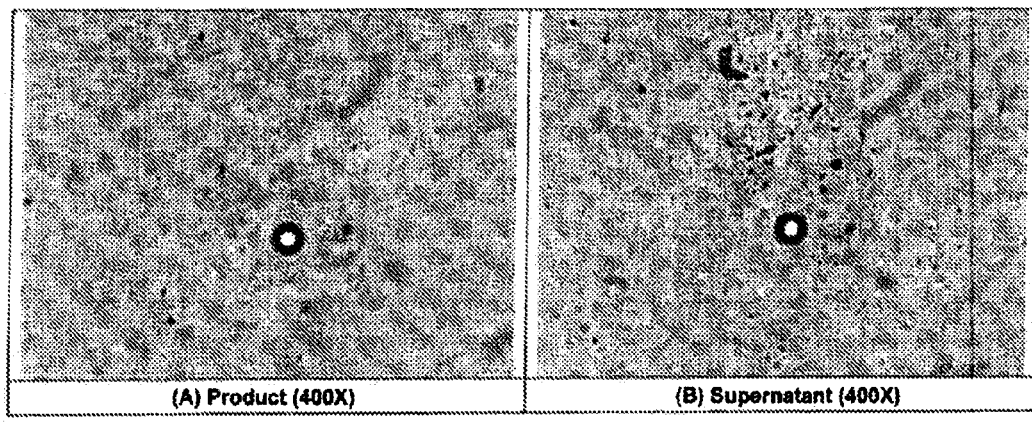
Figure 23a                    Figure 23b
Figures 23a and 23b: Photomicrographs of BPN-24 Polymer Nanospheres Product (A) and Supernatant (B)

NANOTECHNOLOGY FORMULATION OF POORLY SOLUBLE COMPOUNDS

CROSS REFERENCE TO RELATED APPLICATIONS

This application is a continuation of U.S. provisional application Ser. No. 61/402,103 filed Aug. 23, 2010. This application claims priority to such provisional application and incorporates by reference the disclosure therein.

GOVERNMENT SUPPORT

Research leading to this invention was in part funded with Contract No. HHSN2612062209 from the National Cancer Institute, National Institutes of Health, Bethesda, Md., USA,

FIELD OF THE INVENTION

The present invention pertains to articles of manufacture comprising one or more spheres having a diameter of 50 to 500 nanometers which contain poorly soluble compounds and methods for making the same.

BACKGROUND OF INVENTION

Poorly soluble drug candidates are difficult to administer. The drugs are difficult to administer as intravenous drugs. Low concentrations may require long infusion periods which are poorly tolerated and raise the risk of infection. Administered orally, the drugs are often poorly absorbed. There is a need for drug formulations which facilitate the administration of poorly soluble drugs.

SUMMARY OF THE INVENTION

Embodiments of the present invention are directed to articles of manufacture, spheres having a diameter of 50 to 500 nanometers which contain poorly soluble drugs and methods of making such spheres. Embodiments of the present invention have particular application for the following drug candidates and closely related poorly soluble derivatives of such candidates: (i) indole hydrazinecarbothioamide [NSC 73306]; (ii) fenretinide (4HPR) [NSC 374551]; (iii) safingol [NSC 714503]; (iv) 17-allylamino demethoxygeldanamycin (17-AAG) [NSC 330507]; and (v) an aminoflavone drug [NSC 686288].

One embodiment of the article of manufacture comprises a sphere having a diameter of about 50 to 500 nanometers having a shell comprising poly (D,L-lactide-coglycolide polymer) and polycaprolactone containing a poorly soluble drug. The poorly soluble drug is selected from the group consisting of indole hydrazinecarbothioamide [NSC 73306]; fenretinide (4HPR) [NSC 374551]; safingol [NSC 714503]; 17-allylamino demethoxygeldanamycin (17-AAG) [NSC 330507]; and an aminoflavone drug [NSC 686288] and closely related poorly soluble derivatives of such compounds.

One embodiment of the article of manufacture of further comprises a buffer. One embodiment of the present invention features an article of manufacture in which the one or more spheres are lyophilized. In the event the spheres contain a buffer and are lyophilized, it is understood that the volatile components of the buffer are removed and the salts and other non-volatile components remain.

Embodiments of the present invention feature poly(D,L-lactide-coglycolide polymer) which can be present in a ratio of 75:25 to 25:75 lactide-glycoside, or 60:40 to 40:60, or about 50:50.

Embodiments of the present invention feature a buffer having an alcohol. The alcohol has a concentration ranging from 1 to 50%. A preferred alcohol is ethanol.

Embodiments of the present invention feature a sphere having a cross linking agent. The cross-linking agent reacts with the polymers. A preferred cross linking agent is polyvinyl alcohol.

A plurality of spheres is used in a quantity to cause a therapeutic effect. A plurality of spheres is held in a dosage form such as inhalers, capsules, gel caps, tablets, pills, powders, suspensions and transdermal patches.

A further embodiment of the present invention is directed to a method of making one or more spheres having a diameter of about 50 to 500 nanometers having a shell comprising poly(D,L-lactide-coglycolide polymer) and polycaprolactone containing a poorly soluble drug selected from the group consisting of indole hydrazinecarbothioamide [NSC 73306]; fenretinide (4HPR) [NSC 374551]; safingol [NSC 714503]; 17-allylamino demethoxygeldanamycin (17-AAG) [NSC 330507] and an aminoflavone drug [NSC 686288] and poorly soluble derivatives of such compounds. The method comprising the steps of forming a mixture of poly(D,L-lactide-coglycolide polymer) and polycaprolactone containing the poorly soluble compound in supercritical, critical or near critical fluid selected from the compounds nitrogen, carbon dioxide, propane, nitrous oxide and fluoridated hydracarbons, injecting said mixture in a stream in a solution comprising a cross-linking agent in a buffer to form one of more spheres having a diameter of 50 to 500 nanometers, or forming a mixture of poly(D,L-lactide-coglycolide polymer) and polycaprolactone in supercritical, critical or near critical fluid selected from the compounds nitrogen, carbon dioxide, propane, nitrous oxide and fluoridated hydracarbons, injecting said mixture in a stream in a solution containing the poorly soluble compound comprising a cross-linking agent in a buffer to form one of more spheres having a diameter of 50 to 500 nanometers and to form one or more spheres having a diameter of about 100 to 500 nanometers having a shell comprising poly(D,L-lactide-coglycolide polymer) and polycaprolactone containing a poorly soluble drug.

Embodiments of the present method include a step of lyophilization of the one or more spheres.

Embodiments of the present invention comprise poly(D,L-lactide-coglycolide polymer) present in a ratio of 75:25 to 25:75 or 60:40 to 40:60 or about 50:50 lactide to glycolide.

Embodiments of the present method feature a poorly soluble drug in the polymers and/or in a buffer. An embodiment of the present method comprises a buffer having an alcohol. The alcohol has a concentration ranging from 1 to 50%. A preferred alcohol is ethanol.

A preferred cross linking agent is polyvinyl alcohol.

Embodiments of the present invention feature critical, supercritical and near critical fluids. A pure compound enters its supercritical fluid region at conditions that equal or exceed both its critical temperature and critical pressure. These critical parameters are intrinsic thermodynamic properties of all sufficiently stable pure component compounds. A compound is a critical fluid at its critical temperature and critical pressure. A near critical fluid is a compound which is not a supercritical fluid under conditions near the critical pressure and near the critical temperature. Carbon dioxide, for example, becomes supercritical at conditions that equal or exceed its critical temperature of 31.1° C. and its critical pressure of 72.8 atm (1,070 psig). In the supercritical or near-critical fluid region, normally gaseous substances, such as carbon dioxide, become dense phase fluids that have been observed to exhibit greatly enhanced solvating power as compared to the gaseous state. At a pressure of 3,000 psig (204 atm) and a temperature of 40° C., carbon dioxide has a density around 0.8 g/cc and behaves very much like a nonpolar organic solvent.

A supercritical, critical or near critical fluid uniquely displays a wide spectrum of solvation power because its density is strongly dependent on both temperature and pressure—temperature changes of tens of degrees or pressure changes by tens of atmospheres can change solubility by an order of magnitude or more. This unique feature facilitates solute recovery, the "fine-tuning" of solvation power and the fractionation of mixed solutes. The selectivity of nonpolar near-critical, critical or supercritical fluid solvents can be further enhanced by the use of small concentrations of polar entrainers or cosolvents such as ethanol, methanol or acetone. In addition to its unique solubilization characteristics, a supercritical fluid possesses other physicochemical properties that add to its attractiveness as a solvent. A supercritical fluid solvent can exhibit a liquid-like density and, at the same time, gas-like properties of viscosity and diffusivity. The latter increases mass transfer rates, significantly reducing processing times. Additionally, the ultra-low surface tension of a supercritical, critical or near critical fluid allows facile penetration into microporous materials, increasing extraction efficiency and overall yields.

The poorly soluble drug does not need to be dissolved in the buffer or in the polymer compositions. The poorly soluble drug may be present as a suspension of nanoparticles. Embodiments of the present invention feature a step of breaking crystalline drugs into small crystals which facilitate suspension in several media or facilitate dissolution. The drug crystals are broken by subjecting large crystals to one or more cycles of placing with a supercritical, critical or near critical fluid and rapidly decompressing.

These and other features and advantages of the present invention will be apparent to those skilled in the art upon viewing the drawings and reading the detailed description that follows.

BRIEF DESCRIPTION OF THE DRAWINGS

FIG. 10 is a photomicrograph of Aminoflavone Nanoparticles After Supercritical, critical or near critical fluid Particle Size Reduction (BPN-16) at a Magnification of 400×;

FIG. 11 is a photomicrograph of aminoflavone nanoparticles after particle size reduction;

FIG. 12 is a photomicrograph of Aminoflavone Nanoparticles After supercritical, critical or near critical fluid Particle Size Reduction (BPN-19) at a Magnification of 200×;

FIG. 14 depicts the solubility of Aminoflavone in DI Water and 1% PVA;

FIG. 15 depicts solubilities of Aminoflavone and 17-AAG in Methanol and Ethanol at 25 degrees Centigrade;

FIG. 18 is a photomicrograph of BPN-13 Polymer Nanospheres Product;

FIG. 19 is a photomicrograph of BPN-14 Polymer Nanospheres Product (400×);

FIG. 20 is a photomicrograph of BPN-18 Polymer Nanospheres Product (400×);

FIG. 23a is a photomicrograph of BPN-24 Polymer Nanospheres Product; and

FIG. 23b is a photomicrograph of BPN-24 Polymer Nanospheres Product Supernatant.

DETAILED DESCRIPTION OF THE INVENTION

Figure 1:
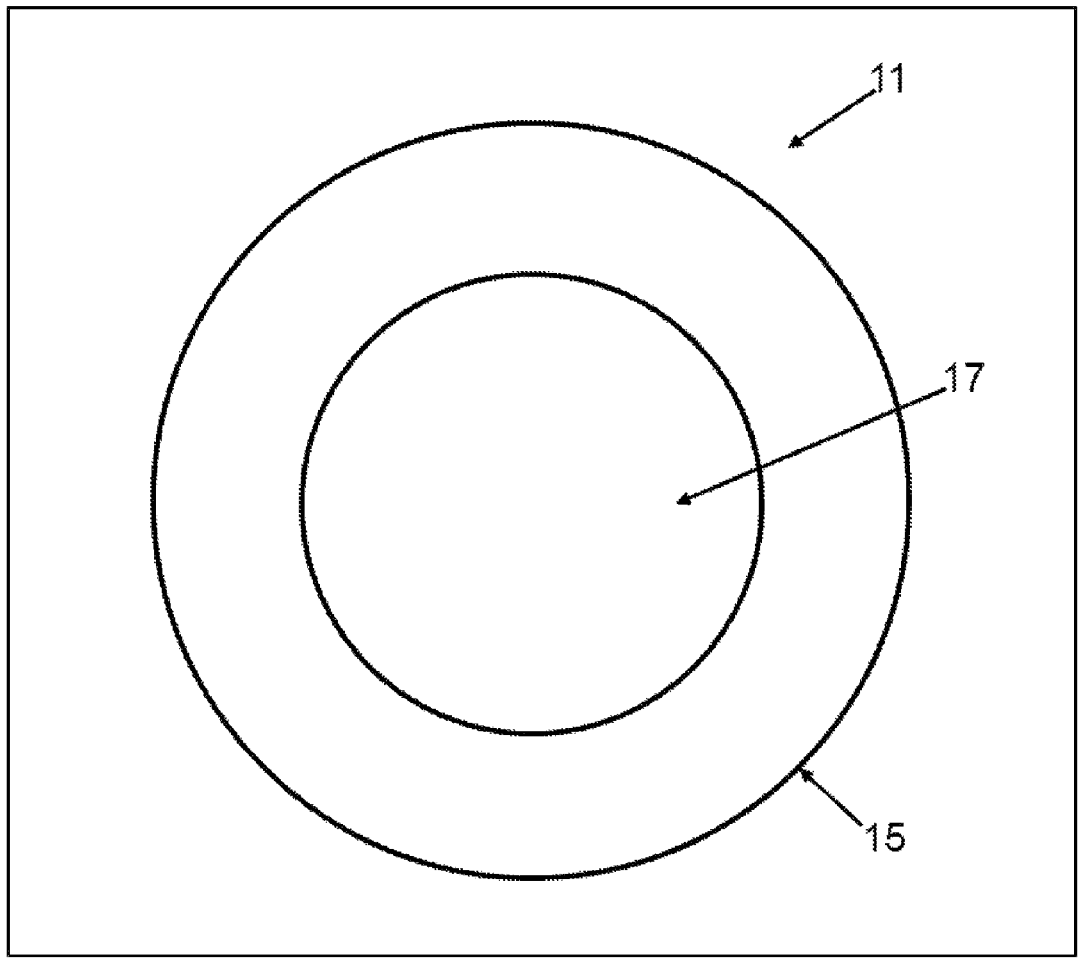
FIG. 1 is a cross sectional view of a sphere embodying features of the present invention.

Turning now to FIG. 1, an embodiment of the present invention directed to the article of manufacture, a lyophilized sphere or particle, generally designated by the numeral 11 is depicted in cross-sectional view. The sphere 11 has a diameter of about 50 to 500 nanometers. Although depicted as a sphere, sphere 11 may not be perfect in its geometric form or shape and may have irregularities. Sphere 11 may have particle-like features. The sphere 11 has a shell 15 comprising a biodegradable polymer which containing a poorly soluble drug. The sphere has an interior 17 which comprises the biodegradable polymer, which may or may not be cross linked, and a poorly soluble drug. The shell 15 is cross-linked. To the extent the buffer is incorporated in the sphere 11, the volatile components are substantially lost upon lyophilization. The buffer in this context refers to the non-volatilized components of the buffer, for example, one or more sugars which may migrate into the shell 15 and interior 17 upon formation.

2.0 Methods and Materials

Figure 2:
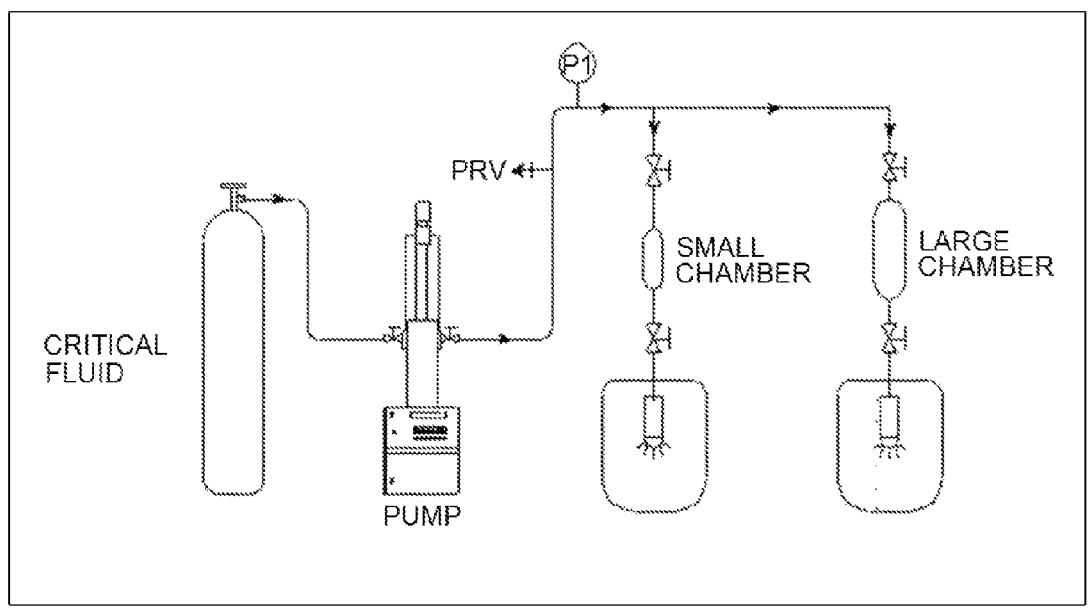
FIG. 2 is a schematic diagram of an apparatus for forming nanoparticles.

Nanoparticles Equipment:

The nanoparticles apparatus is shown in FIG. 2. This apparatus consists of three major components: (1) a supercritical fluid pumping or pressurizing system; (2) contacting chambers, a small chamber used for 100 mg samples and a large one used for 1 gram samples; and (3) depressurization and product recovery receptacles (Ziploc® bags). The desired amount of compound is manually loaded into contact chamber, sealed and connected to the system.

Supercritical, critical or near critical fluid contained in a gas cylinder is supplied through a high-pressure pump to the contact chamber. Pressure is indicated by pressure indicator, PI. Once the contact chamber has been pressurized, the anti-cancer compound and Supercritical, critical or near critical fluid™ will be allowed a certain amount of contact time. After the desired contact time, the valve on the exit of the contact chamber is opened quickly, i.e., in less than 1 second, causing rapid depressurization of Supercritical, critical or near critical fluid™ with entrained nanoparticles in the depressurization receptacle. Depressurization is carried out through a nozzle device that includes an impingement surface to increase mechanical shear by deflecting the discharging material. After depressurization, the nanoparticles are collected from the depressurization receptacle for analysis and further processing.

Figure 3:
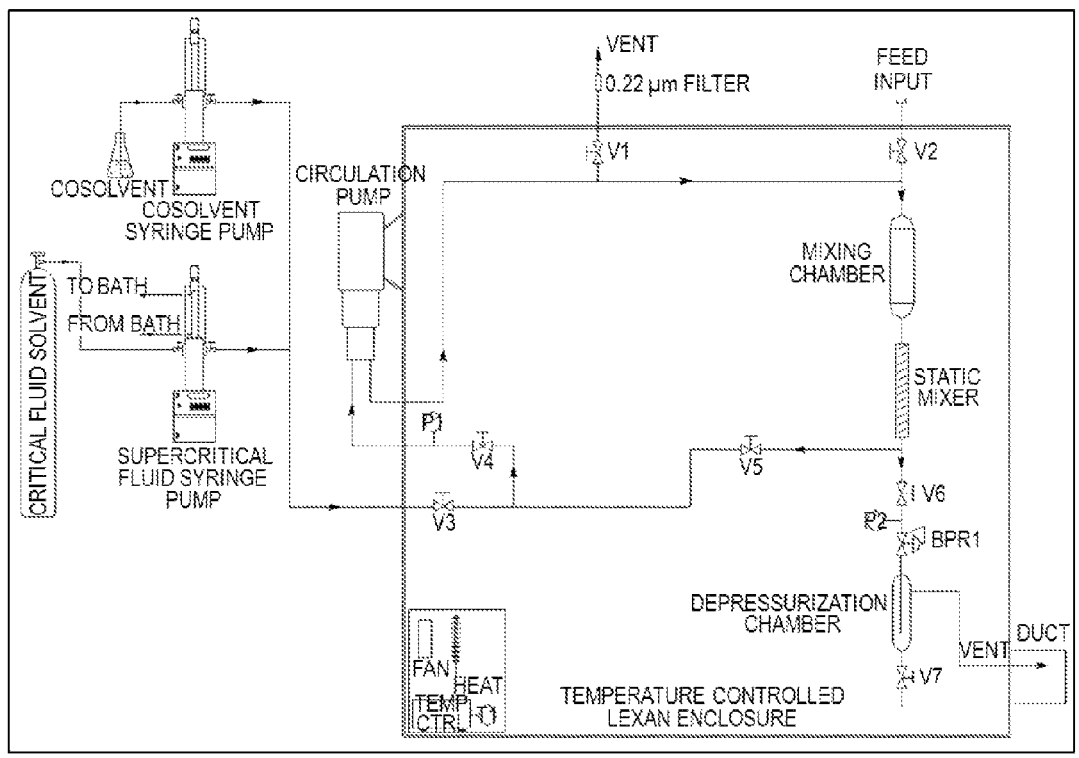
FIG. 3 depicts a supercritical, critical or near critical fluid Polymer Nanospheres Apparatus.

Polymer Nanospheres Equipment:

The Supercritical, critical or near critical fluid polymer nanospheres apparatus is shown in FIG. 3. This apparatus consists of a mixing chamber, a solids chamber for containing the polymer, a high pressure circulation pump, a static in-line mixer, back pressure regulators (BPR), injectors and a sample collection chamber all contained in a temperature controlled chamber. External to this chamber, two syringe pumps (Isco, Inc., Lincoln, Nebr.), are used for delivery of the supercritical fluid, cosolvent w/wo nano-particles. The mixing chamber, solids chamber and circulation pump are connected in a high-pressure circulation loop with a total volume of approximately 160 ml.

The outlets of the supercritical fluid and cosolvent syringe pumps are connected at a mixing tee and fed into the high-pressure circulation loop at the entrance of the static in-line mixer that is upstream of the solids chamber.

The system is maintained as a closed system. The entire apparatus up to the backpressure regulators is designed to operate up to 5,000 psig and 60° C. The apparatus will be cleaned in-place by washing with a series of solvents including bleach, caustic and dilute hydrochloric acid, and then sterilized in-place with an ethanol/water (70/30) mixture.

Figure 4:
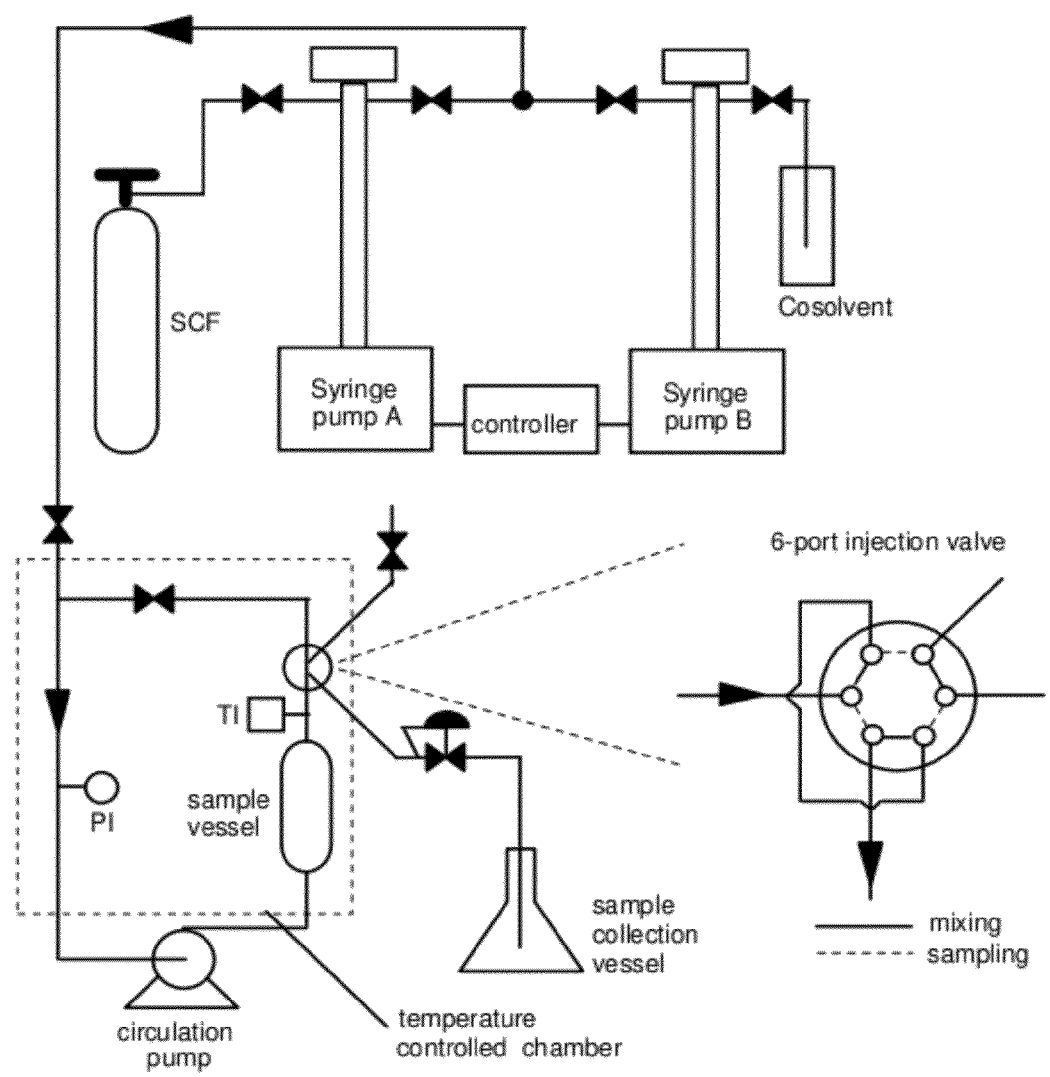
FIG. 4 depicts a supercritical, critical or near critical fluid Solubility (SOL) Apparatus.

Supercritical, Critical or Near Critical Fluid Solubility Equipment:

The solubility experiments were conducted in a Supercritical, critical or near critical fluid™ solubility (SOL) apparatus shown as FIG. 4. The solubility apparatus mainly consists of a sample vessel, a circulation pump and a 6-port injection valve, all contained in a temperature-controlled chamber. An Isco SFX 2-10 supercritical fluid extractor (Isco, Inc., Lincoln, Nebr.) with integral heating/control system is utilized as the sample vessel. Two Isco syringe pumps (Isco, Inc., Lincoln, Nebr.), model 260D and 100D, are used for supercritical fluid and cosolvent delivery, respectively. Supercritical, critical or near critical fluid™ solubility experiments were performed in accordance with Aphios' Standard Operating Procedure #P96014.

Figure 5:
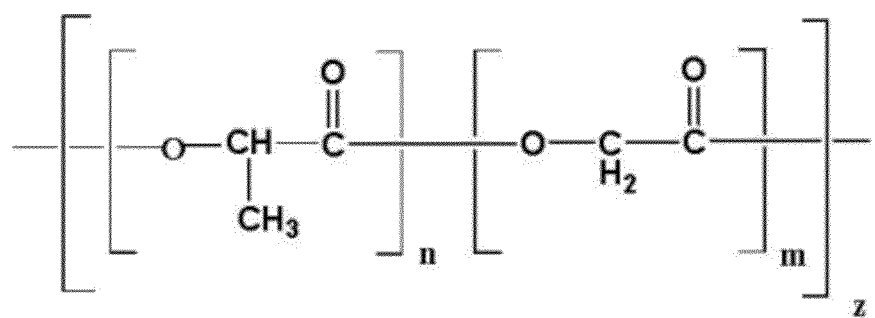
FIG. 5 is a chemical representation of PLGA.

Biodegradable Polymers:

The biodegradable polymer used was Resomer® RG 502 PLGA (Boehringer Ingelheim KG), Lot #200727, with an inherent viscosity of 0.16-0.24 dL/g and glass transition temperature range of 40-55° C. This poly (lactic-co-glycolic acid) PLGA polymer (FIG. 5) is a 50:50 mixture of poly (lactic acid) PLA and poly (glycolic acid) (PLG).

Supercritical, Critical or Near Critical Fluid:

Supercritical, critical or near critical fluid™ utilized include carbon dioxide, nitrogen, trifluoromethane (Freon-23) and chlorodifluoromethane (Freon-22). The physical properties of these Supercritical, critical or near critical fluid™ are listed in Table 1.

TABLE 1

Physical Properties of Selected Supercritical Fluid Solvents

| Supercritical, critical or near critical fluid ™ | Formula | BP (° C.) | $P_{vap}$ (psia @ 25° C.) | $T_c$ (° C.) | $P_c$ (psia) | Dipole Moment (Debyes) |
|---|---|---|---|---|---|---|
| Carbon dioxide | $CO_2$ | −78.5 | 860 | 31.1 | 1070 | 0.0 |
| Nitrogen | $N_2$ | −195.7 | 593 | −146.9 | 491 | 0.0 |
| Freon-23 | $CHF_3$ | −82.1 | 701 | 25.9 | 4.73 | 1.6 |
| Freon-22 | $CHClF_2$ | −40.8 | 166 | 96.1 | 720 | 1.4 |

Figure 6:
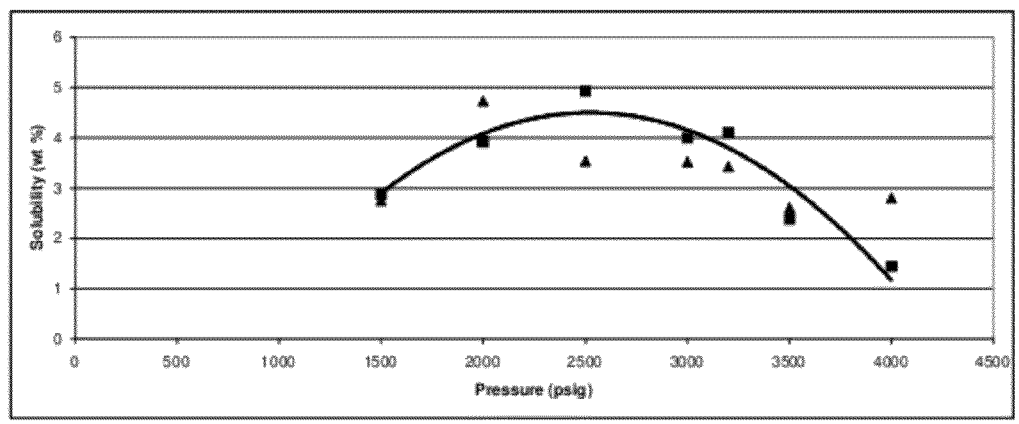
FIG. 6 depicts Solubility of Biodegradable PLGA Polymers in supercritical, critical or near critical fluid.

BP = Normal boiling point;
$P_{vap}$ = Vapor pressure;
$T_c$ = Critical Temperature;
$P_c$ = Critical Pressure Solubility of Biodegradable PLGA Polymers in Supercritical, Critical or Near Critical Fluid:

Conditions for optimum polymer solubilization in a supercritical, critical or near critical fluid stream depend on several parameters including the composition and molecular weight of the polymer, supercritical, critical or near critical fluid type, pressure and temperature, and for nonpolar fluids such as carbon dioxide, cosolvent type and concentration. We have measured the solubilities of PLGA polymers in several different supercritical, critical or near critical fluids. Selected data are listed in Table 2 and shown in FIG. 6.

Near-critical propane is only very slightly polar, having a dipole moment of 0.084 Debyes—a factor that may also contribute to its solvation selectivity for PLGA. Propane is, however, flammable and operationally cumbersome to work with in a manufacturing environment (requiring explosion proof equipment and facilities) even though it is considered GRAS. Octafluoropropane is considered a substitute for propane. The combination of its structure and fluorination will contribute to its solvation selectivity for PLGA. Difluorochloromethane, Freon-22, is an attractive solvent because of its capability to dissolve PLGA. Freon-22 is, however, chlorinated and has an ozone depletion factor of 0.05. Freon-22 will be banned from use in 2020 according to the 1988 Montreal protocol. Freon-23, trifluoromethane, is an excellent candidate since it is not chlorinated and has a much lower critical temperature than Freon-22. Freon-23 is, however, quite expensive compared to Freon-22. For large-scale manufacturing, it is desirable to recover and recycle the supercritical, critical or near critical fluid so there should be a minimal cost impact if orthofluoropropane or Freon-23 is used.

TABLE 2

Solubilities of Resomer ® RG 502 PLGA in Supercritical Fluid Solvents (3,000 psig and 30° C.)

| Supercritical, critical or near critical fluid ™ | Formula | $T_c$ (° C.) | $P_c$ (psia) | Dipole Moment (Debyes) | Solubility (mg/ml) |
|---|---|---|---|---|---|
| Propane | $C_3H_8$ | 96.7 | 601.6 | 0.084 | 1.45 |
| Orthofluoropropane | $C_3F_8$ | 71.9 | 388.7 | NA | NM |
| Freon-22 | $CHClF_2$ | 96.0 | 707.2 | 1.4 | 8.98 |
| Freon-23 | $CHF_3$ | 26.1 | 700 | 1.6 | 0.20 |

Particle Size Measurements:

Particle sizes and distributions of the formulations were determined by laser beam interferometer, using a Coulter N4MD submicron particle size analyzer with a range of 30 Angstroms to 3 microns. This technique utilizes photon correlation spectroscopy of the Brownian motion of particles suspended in a liquid to determine the particle size. Multiple-angle detection on the N4M allows for better characterization of polydisperse samples. These analyses will provide: (i) unimodal size analyses that have only mean size and standard deviation; (ii) size distribution analyses that yield information about polydispersity of the sample; and (iii) for the Coulter N4MD Plus, "fingerprint," a procedure that uses the multiple angle measurement provided by the instrument to detect contamination of a sample by particles larger or smaller than the main distribution. Basically, the nanoparticles were suspended in a solvent at a dilution that had a light scattering intensity of around $2\times10^5$ counts per second at 20° C. and the measurement was made.

Anticancer Compounds:

The following anticancer compounds were provided by the National Cancer Institute.
1. NSC 73306—Indole Hydrazinecarbothioamide
2. NSC 374551—Fenretinide (4HPR)
3. NSC 714503—Safingol
4. NSC 330507—17-Allylamino Demethoxygeldanamycin (17-AAG)
5. NSC 686288 Aminoflavone S2: NSC 374551—Fenretinide (4HPR)
Fenretinide (4HPR), MW=391.55, is a synthetic retinoid that is much less toxic than natural retinoids for use in breast cancer.

S3: NSC 714503—Safingol
Safingol, MW=302, has been shown to potentiate the antitumor effect of various chemotherapeutic agents.

S4: NSC 330507—17-Allylamino Demethoxygeldanamycin (17-AAG)
17-Allylamino Demethoxygeldanamycin (17-AAG), MW=586, is an analog of geldanamycin that has demonstrated in vitro activity against chemorefractory tumor with novel biological actions.

S5: NSC 686288 Aminoflavone
NSC 686288 has demonstrated good differential activity in NCI's 60-cell line screen with particularly prominent activity against the CaKi-1 and A498 renal, MCF-7 breast and OVAR-5 ovarian cancer cell lines. In vivo, NSC 686288 treatment produced complete regressions and/or tumor-free animals against the respective renal cancer xenograft models. Intravenous treatments of NSC 686288 were shown to be less toxic than its prodrug NSC 710464D, a lysyl dimethanesulfonate salt on a molar-equivalent basis. This was probably due to the greater solubility of the prodrug. Intraperitoneal treatments rendered similar levels of efficacy for both the parent and prodrug at somewhat lower doses.

NSC 686288 is readily soluble in DMSO, and exhibited greatest aqueous solubility (650 ng/mL) at pH 10 (glycine buffer) [Mayo Clinic, 1998]. At pH 4 and pH 7, the solubility of NSC 686288 was 126-188 ng/mL.

Difficulties were encountered in initial microsomal experiments (non-linearity of reaction with [drug] or [enzyme] and low drug discovery in controls) was found to be due to adsorption of NSC 686288 to glass tubes. As such, experiments with cDNA-expressed human CYP450s were repeated using silanized plastic microcentrifuge tubes.

3.0 Analytical Chemistry
HPLC Analysis of Selected NCI Standards
Objective:
To do preliminary HPLC-PDA runs as a starting point for HPLC method development.
Sample Identification
1. NSC 73306—Indole Hydrazinecarbothioamide
2. NSC 374551—Fenretinide (4HPR)
3. NSC 714503—Safingol
4. NSC 330507—17-Allylamino Demethoxygeldanamycin (17-AAG)
5. NSC 686288—Aminoflavone Drug Sample Rejection
Sample 1 was put on hold by the TPO. Sample 3 has no chromophores in the wavelength region of 190-600 nm and therefore cannot be done using a PDA detector. Sample 3 was weighed to obtain solubility information.

Gradient HPLC System
Column=Phenomenex Luna C18(2) 4.6 mm×15 cm.
Buffer Concentrate: 100 mL triethylamine plus 80 mL phosphoric acid to 1 L Water.
Aqueous Buffer: 10 mL of Buffer Concentrate to 1000 mL with water.
Temperature=30° C. Flow=1.5 mL/min, Injection Volume=20 µL
Gradient: A=Aqueous Buffer B=100% ACN
0% B to 100% B in 60 minutes
100% B to 0% B in 2 minutes
Equilibrate for 13 minutes The following gradient scans were run without baseline correction.

Sample 2 elutes as a pure peak. The retention time corresponds to an acetonitrile percentage of approximately 79%. The small peaks at 34 and 65 minutes appear in the 100% methanol scan and were removed later using baseline correction.

Isocratic HPLC Scans using 80% ACN/Buffer as the Mobile Phase.
Column=Phenomenex Luna C18(2) 4.6 mm×15 cm.
Buffer Concentrate: 100 mL triethylamine plus 80 mL phosphoric acid to 1 L Water.
Aqueous Buffer: 10 mL of Buffer Concentrate to 1000 mL with water.
Temperature=30° C. Flow=1.5 mL/min, Injection Volume=20 µL
Solvents: A=25% ACN in Buffer B=100% ACN
Use 26.67% A and 73.33% B to make 80% ACN
PDA Resolution=3.6 nm
Sample 2: Diluted 100 µL to 1,000 µL in Methanol to Yield C=16.3 mg/100 mL The HPLC scan shows a symmetric peak at 7.054 minutes and two small impurity inflections eluting at approximately 6.4 and 6.7 minutes. These two impurities are easily seen in the contour plot—which is presented in exponential mode to detect small changes in absorbance.

Based on the retention time, an acetonitrile concentration of 80% would be appropriate for this compound. The UV maximum is at approximately 370 nm.

Sample 4: Diluted 100 µL to 1,000 µL in Methanol to Yield C=22.0 mg/100 mL

The HPLC scan shows a symmetrical peak with a retention time of 2.018 minutes. This is too close to the solvent front so an acetonitrile concentration less than 80% would be required. % ACN in the range of 50% to 60% should be considered. The compound has large absorbance maxima at approximately 242 nm and 334 nm and a smaller local absorbance maximum at 540 nm.

Sample 5: Diluted 100 µL to 1,000 µL in Methanol to Yield C=4.8 mg/100 mL

The HPLC scan shows a symmetrical peak with a retention time of 1.978 minutes, which like sample 4, is too close to the solvent front and for an isocratic system, an acetonitrile concentration in the range of 50% to 60% should be considered. The compound has an absorbance maximum at approximately 345 nm.

Title: Approximate Determination of Aminoflavone in Suspension
Application: Suspensions of Aminoflavone and Resomer RG 502 in Aqueous Solutions of PVA.
HPLC Method
Column: Phenomenex Luna C18(2), 15-cm×4.6 mm.
Buffer Concentrate (BC): 100 mL $Et_3N$×80 mL 85% $H_3PO_4$ to 1000 mL with water.
Mobile Phase A=250 mL ACN+10 mL of BC to 1000 mL with water.
Mobile Phase B=100% ACN
Isocratic Mixture: 53% Phase A and 47% Phase B.
Alternatively, use 60% Acetonitrile with 3-mL Buffer Concentrate/1000 mL
Flow=1.5 mL/min
Temperature=30° C.
Wavelength=330 nm
Injection Volume=20 µL
Standard Concentration: 10.0 mg/100 mL
Procedure
1. Determine the volume of the polymer suspension (V mL).
2. Swirl the sample rapidly and then quickly withdraw 2 mL of suspension.
3. Combine the 2 mL with 10 mL of 100% Methanol in a small vial.
4. Sonicate to dissolve. Then assay by HPLC to obtain C (mg/100 mL).
5. Total milligrams aminoflavone=V×12/2×C/100
Note: This analytical method will give only an approximate result since withdrawal of 2 mL from a rapidly settling suspension can only lead to high variability in the sampling.
Preparation of the Standard
1. Weigh approximately 25 mg of aminoflavone Standard to 0.1 mg into an aluminum dish. Quantitatively transfer to a 100 mL volumetric flask with methanol, bring to volume with methanol, sonicate to dissolve, and mix well to form the stock standard solution.
2. Dilute the stock standard solution 10 mL to 25 mL to obtain the 10-mg/100 mL standard solution. Use this solution to calibrate the HPLC.
3. If a standard curve is required to be run, the following dilutions are suggested:
From Stock: 5, 10, 15, and 20 mL each to 25 mL with methanol.
From the Dilutions: Dilute each 2/10 to reduce the above concentration by 5.
Low Point: Dilute the 1-mg/100 mL solution 5/10 with methanol.

TABLE 3

Aminoflavone Standard Curve

| Conc. (mg/100 mL) | HPLC Response |
|---|---|
| 0.0 | 0.000 |
| 0.5 | 0.471 |
| 1.0 | 0.979 |
| 2.0 | 1.836 |
| 3.0 | 2.854 |
| 4.0 | 3.769 |
| 5.0 | 4.949 |
| 10.0 | 10.000 |
| 15.0 | 14.556 |
| 20.0 | 19.499 |
| 25.0 | 24.233 |

Title: Determination of Aminoflavone and Resomer RG 502 in Nanospheres
Analytical Methods
A. Gravimetric: For samples containing a large amount of polymer and a relatively small amount of encapsulated material, simply weighing the dry product will give the sum of the polymer plus the encapsulated material. If the encapsulated material can be determined by HPLC, then the Polymer can be obtained by difference.
B. HPLC: The polymer contains ester groups and will therefore have a weak but usable absorbance in the 205 nm region. If a chromatographic system can be found in which essentially the entire polymer elutes close to the solvent front, then an HPLC method could be developed.
Procedure
1. Select a sample consisting of nanoparticles suspended in 10-100 mL of solvent.
2. Determine the tare weight of a 50-mm/0.45 micron Nylon 66 filter disc.
(Handle carefully as these discs are fragile.)
3. Filter the suspension through the disc. Do not rinse.
4. Collect the filtrate, measure its volume, transfer to a storage vessel, assay by HPLC, and determine its solids content by evaporating 5 mL in a tarred Aluminum boat at a temperature not to exceed 100° C. Do the final drying in a vacuum oven at room temperature for 1 hour.
5. Carefully transfer the filter disc to a watch glass, cover with a second watch glass, and dry in the vacuum oven for 1 hour. Weigh the dried disc to determine the weight of the nanoparticles. Assay a portion of this solid material for the aminoflavone.

4.0 Experimental Results
4.1 Nanoparticles Experiments

Based on preliminary data with other inorganic molecules (e.g., paclitaxel, zinc carbonate and albuterol sulfate), nitrogen was the most effective Supercritical, critical or near critical fluid™ tested. Nitrogen is an excellent generic candidate since it is inexpensive and very inert. Nitrogen was likely the most effective Supercritical, critical or near critical fluid™ tested because of its molecular size, which allows diffusion and penetration into molecular aggregates. In preliminary studies, the optimum pressure was defined as being between 3,000 and 4,000 psig for carbon dioxide.

Our previous research has shown a strong correlation between moisture content and Supercritical, critical or near critical fluid™ comminution efficiency. Our research also indicates that the combination of a water-saturated particle followed by freezing appears to provide optimum conditions for Supercritical, critical or near critical fluid™ comminution.

The latter strongly suggests that freeze-fracture may be a necessary condition for optimum Supercritical, critical or near critical fluid™ penetration of the target particle. After snap freezing at a liquid $N_2$ temperature of 77° K (−196° C.), the closed system will be warmed up to room temperature thereby increasing the pressure. This pressure increase will be supplemented, if necessary, by applying pressure more efficiently to the liquid $N_2$ or more conveniently to nitrogen at room temperature. The second important aspect of temperature appears to be directed to the optimum penetration of the target particle by the Supercritical, critical or near critical fluid™. Theoretically, optimum penetration should be achieved at temperatures that favor high diffusion rates.

Nanoparticles Experiments, BPN-01, BPN-02, BPN-05:
Three nanoparticles experiments were conducted—two with surrogate compounds and one with aminoflavone prodrug (Sample 5). In general, the poorly water-soluble anticancer compound was first saturated with water by placement in the vapor generated by a 39° C. temperature water bath for 60 minutes. The water-saturated sample was then frozen in a −80° C. freezer for 60 minutes. The frozen particles were then placed in the chamber of the nanoparticles apparatus (FIG. 2) and contacted with nitrogen at 3,000 psig for 60 minutes to ensure maximum saturation of the hydrophobic anticancer compound by the SFS. The materials were then rapidly depressurized, discharging the chamber contents into a collection container. The experiments were conducted following Standard Operating Procedure SOP #APH-S0603 and Drawing #9706-001 Rev 2 in Appendix C. The results are summarized in Table 4.

The nanoparticles results of surrogate compound 1 in BPN-01 was within the anticipated range, while the results of BPN-02 on surrogate compound 2 was just outside the expected range. The aminoflavone sample nanoparticles in BPN-03 were much larger than expected suggesting that some modification of process parameters will be required for this compound.

HPLC analyses of the surrogate compounds and aminoflavone did not indicate any product degradation of the treated materials versus the untreated controls.

TABLE 4

Nanoparticles Experiments (BPN-01, BPN-02, BPN-05)

| Expt. No. | Sample | Before | After |
|---|---|---|---|
| BPN-01 | Surrogate Compound 1 | 10-25 μm (majority) and 20-50 μm, (flat square/rectangular shape) | 1-3 μm (uniform), (flat square/rectangular shape) |
| BPN-02 | Surrogate Compound 2 | Width-5 to 12 μm, length-25 to 150 μm, (cylindrical/rod shaped) | 5 to 7 μm, (flat square/rectangular shape), few 1 × 7 μm slivers |
| BPN-05 | Amino-flavone Drug | Irregular crystal shapes, rectangular, needle, and shafts. 25 μm to 150 μm, a few up to 700 μm | Shapes are more regular, square, 3.5 μm to 12 μm, several around 20 μm, sample clumpy |

Several different solutions were evaluated for suspending the nanoparticles in order to measure their size in the Coulter N4MD Submicron Particle Analyzer. In previous research we had determined that a 95% methylene chloride and 5% acetone solution was an ideal mixture for bovine serum albumin (BSA) powder and could also be utilized for insulin. The purpose of suspending the nanoparticles was two fold, for: (1) measurement of particle size distribution; and (2) pumping into a polymer-rich Supercritical, critical or near critical fluid™ stream as part of the polymer nanoencapsulation strategy. Since we preferred not using relatively toxic organic solvents in the encapsulation process, we evaluated several different solutions for suspending the nanoparticles utilizing surrogate compound No. 1. The results are summarized in Table 5.

TABLE 5

Visual Observations and Particle Sizes of Surrogate Compound No. 1 in Different Solutions

| Sample No. | Mixture | Visual Observation | Particle Size (nm) | Dust (%) |
|---|---|---|---|---|
| 0 | 0.5 micron nylon spheres in DI H₂O | Solution crystal clear | 547 | 0 |
| 1 | 0.1% PVA in DI H₂O | Solution milky with particles at top and bottom of container | 1,430 | 0 |
| 2 | 1.0% PVA in DI H₂O | Solution slightly milky with some particles at top but most at bottom of container | 1,360 | 0 |
| 3 | 0.1% PEG in DI H₂O | Solution almost clear, very few particles observed at top | 854 | 6 |
| 4 | 1% PEG in DI H₂O | Solution almost clear, few particles observed at top | 1,040 | 0 |
| 5 | 0.1% Triton X-100 in DI H₂O | Solution almost clear, many particles observed at bottom | 1,260 | 0 |
| 6 | 1.0% Triton X-100 in DI H₂O | Solution milky with many particles observed at bottom | 1,300 | 0 |
| 7 | 95% Methylene Chloride; 5% Acetone | Solution crystal clear with no particles observed | 1,370 | 0 |

Figure 7:
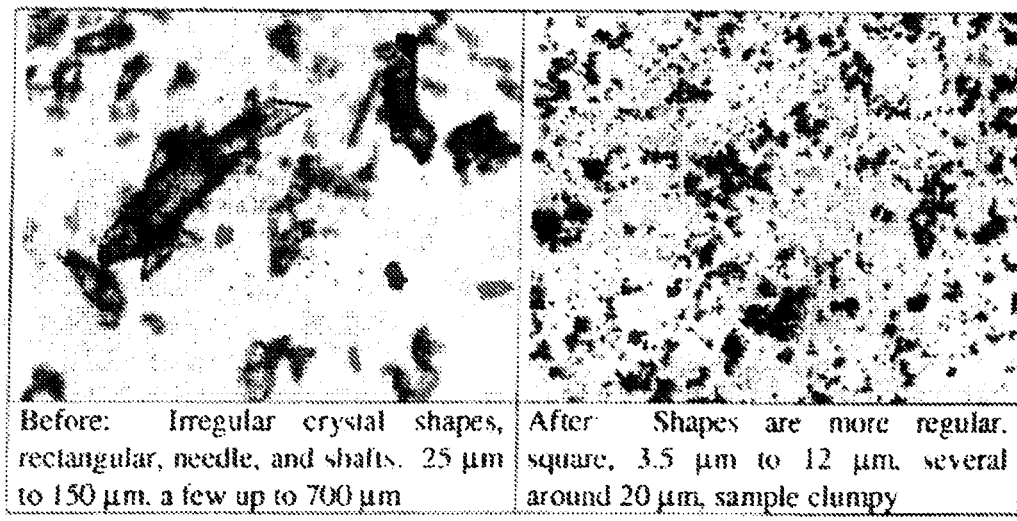
FIG. 7a is a of photomicrograph of Aminoflavone Particles before supercritical, critical or near critical fluid Particle Size Reduction at a magnification of 200×.
FIG. 7b is a of photomicrograph of Aminoflavone Particles after supercritical, critical or near critical fluid Particle Size Reduction at a magnification of 200×.

Photomicrographs of aminoflavone particles in experiment BPN-05 before comminution (left) and after supercritical, critical or near critical fluid particle size reduction (right) is shown in FIGS. 7a and 7b at a magnification of 200×.

Figure 8:
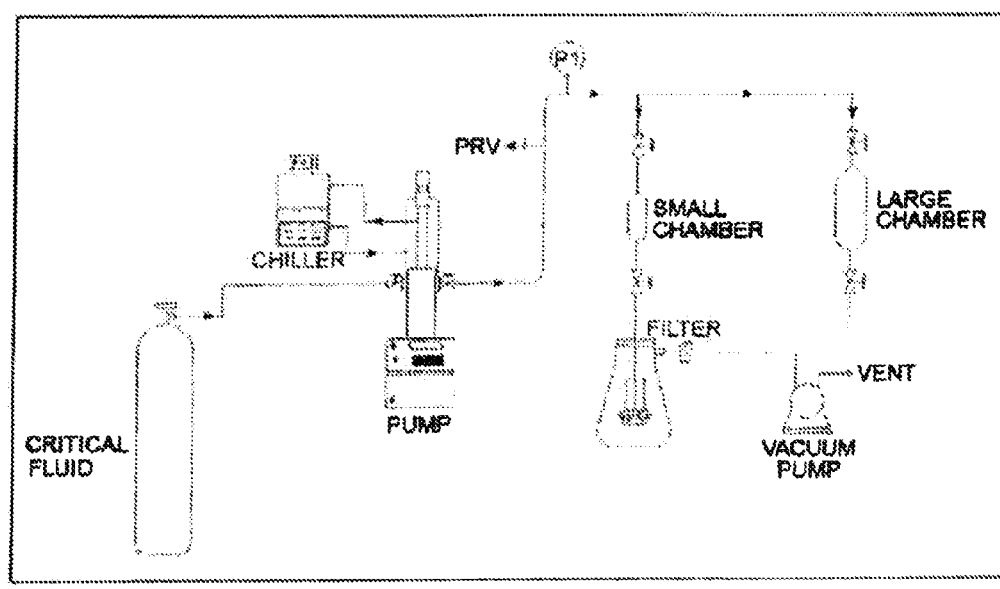
FIG. 8 depicts a drawing of a Modified Supercritical, critical or near critical fluid Nanoparticles Apparatus.
Figure 9:
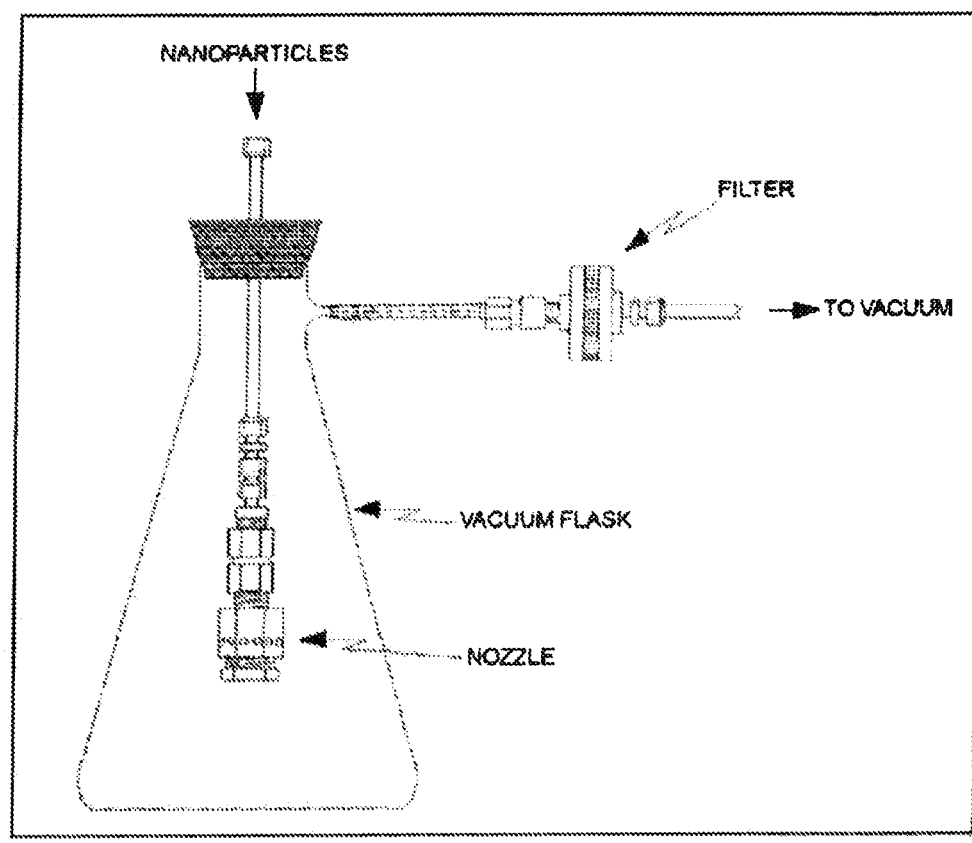
FIG. 9 depicts a drawing of Modified Collection Flask

Nanoparticles Experiments, BPN-09, BPN-10, BPN-11:

In the three experiments listed in Table 5, the nanoparticles recovery efficiencies were very low because a significant amount of particles became embedded in the Ziploc® plastic bag. In order to improve the recovery efficiencies, a 2-Liter vacuum flask was used as the depressurization and product recovery chamber as shown in FIG. 8. The side port was attached to a filter and a vacuum pump. A detailed schematic of this modification is shown in FIG. 9.

The following procedures pertain to all three (3) runs: The material was subjected to a hydration process consisting of being placed in a water bath enclosure for one (1) hour at 39° C. The material was then subjected to a freezing process for one (1) hour in an −80° C. freezer. The Nanoparticle generation process consists of placing the material inside a chamber under high pressure for a predetermined time period, then rapidly depressurizing the chamber contents into a collection container. Conditions were the same as those used in the previous runs.

Three experiments were conducted with the modified nanoparticles apparatus. The results are summarized in Table 6. In BPN-09, a Whatman #42, 2.5 μm 42.5 mm, filter paper was used; in BPN-10 & 11 a Pall Life Science, 0.45 μm nylon, 47 mm filter was used. On runs BPN-10 and BPN-11, a vacuum pump was connected to the filter outlet and was operational during chamber discharge and for a period of thirty (30) minutes following discharge.

TABLE 6

Nanoparticles Experiments (BPN-09, BPN-10, BPN-11)

| Expt. No. | Sample | Before | After |
|---|---|---|---|
| BPN-09 | Fenretinide (4HPR) | Crystals are yellow and rectangular 6 × 19 μm or less. Many around 4 × 9 μm and clumped together. | Crystals are now on the square side measuring 1 to 3 μm and clumped. |

TABLE 6-continued

Nanoparticles Experiments (BPN-09, BPN-10, BPN-11)

| Expt. No. | Sample | Before | After |
|---|---|---|---|
| BPN-10 | Safingol | Very large white crystals, rectangular, 300 × 550 um and 250 × 750 μm, and square, up to 400 μm. | Round and square shaped. Majority 1-2 μm, a few up to 5 μm. |
| BPN-11 | Allylamino Demethoxy-geldanamycin (17-AAG) | Crystals are red and rectangular, two (2) common sizes: 19 × 50 μm & 25 × 100 μm or less. | Round and square shaped. Majority 1-2 μm, a few 5-9 μm |

The products appeared to have a high degree of static electricity in that they clung to the inside surfaces of the flask and the outer surfaces of the nozzle. They were recovered with a small stream of de-ionized (DI), 0.22 micron filtered water.

Particle sizes of the feeds and products from these runs were measured in the Coulter N4MD sub-micron particle analyzer instrument according to SOP #P96004 in Appendix D. The instrument was first calibrated with 0.5 micron latex beads (see Figure E-1 in Appendix E).

Chemical Analysis of BPN-09:

Three samples in aluminum weigh boats with contents weight of 0.4 to 0.5 mg was provided. To obtain the assay solution, each boat was placed in a sonicator bath filled to a height of 3 mm with water. Ten milliliters of methanol was pipetted into the boat and the sonicator was turned on for 20 seconds. The yellow residue in the boat dissolved completely in less than 5 seconds. After sonication, the sample was drawn back into the 10 mL pipette and transferred to a 20 mL scintillation vial to await HPLC assay.

The Standard:

S2: NSC 374551—Fenretinide (4HPR)

16.3 milligrams of this standard was dissolved in 10 mL of methanol to form a test solution. The following system was used for analysis:

Gradient HPLC System:

Column=Phenomenex Luna C18(2) 4.6 mm×15 cm.

Buffer Concentrate: 100 mL triethylamine plus 80 mL phosphoric acid to 1 L Water.

Aqueous Buffer: 10 mL of Buffer Concentrate to 1000 mL with water.

Temperature=30° C. Flow=1.5 mL/min Injection Volume=20 μL

Gradient: A=Aqueous Buffer B=100% ACN

0% B to 100% B in 60 minutes

100% B to 0% B in 2 minutes

Equilibrate for 13 minutes

Standard 2 (S2) eluted as a pure peak. The retention time corresponds to an Acetonitrile percentage of approximately 79%.

To observe decomposition products that move closely with S2, an isocratic was set up using 85% ACN with buffer (ACNB) and the old standard solution that had been stored at room temperature on the laboratory bench was injected. The initial scan showed decomposition products and the separation between these products and S2 was improved by changing the mobile phase from 85% ACNB to 80% ACNB as shown below.

HPLC Calibration:

The response factor of the freshly prepared standard (Peak Area/Concentration) was applied to the peaks of the degraded standard to obtain an accurate concentration for S2 and an approximate concentration for decomposition products A, B, and C which is based on the S2 response factor at 362 nm—the wavelength used for the isocratic assay.

Decomposition of the BPN-09 Product

All BPN-09 samples showed 13-14% impurity "C" and trace amounts of "A", and "B". Sample BPN-09-01 is typical of BPN-09-02 and BPN-09-03.

TABLE 7

Assay of the three BPN-09 Samples:

| BPN-09 | C(mg) | S2(mg) |
|---|---|---|
| 1 | 0.0086 | 0.0545 |
| 2 | 0.0088 | 0.0544 |
| 3 | 0.0089 | 0.0547 |

Chemical Analysis of BPN-11:

Three samples in aluminum weigh boats with contents weight of 0.4 to 0.5 mg were provided for analysis. To obtain the assay solution, each boat was placed in a sonicator bath filled to a height of 3 mm with water. Ten milliliters of methanol was pipetted into the boat and the sonicator was turned on for 5 seconds. The pink residue in the boat dissolved completely in less than 2 seconds. After sonication, the sample was drawn back into the 10 mL pipette and transferred to a 20 mL scintillation vial to await HPLC assay.

The product was 60 mL of aqueous slurry. The product was swirled rapidly to suspend the particles and then 1.00 mL of slurry was delivered to a 10 mL volumetric flask and methanol was added to bring the sample solution to volume. Sonication produced rapid solution of all particles.

The Standard:

S4: NSC 330507: 17-Allylamino Demethoxydeldanamycin (17-AAG)

On Jan. 8, 2007, 22.0 milligrams of this standard was dissolved in 10 mL of methanol to form a test solution. The following system was used for analysis:

Gradient HPLC System

Column=Phenomenex Luna C18(2) 4.6 mm×15 cm.

Buffer Concentrate: 100 mL triethylamine plus 80 mL phosphoric acid to 1 L Water.

Aqueous Buffer: 10 mL of Buffer Concentrate to 1000 mL with water.

Temperature=30° C. Flow=1.5 mL/min Injection Volume=20 μL

Gradient: A=Aqueous Buffer B=100% ACN

0% B to 100% B in 60 minutes

100% B to 0% B in 2 minutes

Equilibrate for 13 minutes

Using the gradient system, S4 eluted as a pure peak at an Acetonitrile concentration of approximately 55%. Based on this, an isocratic system was set up using a net ACN concentration of 55%. This was done using a solvent mixer with 25% ACN in the "B" line and 100% ACN in the "C" line. We used 60% "B-line" and 40% "A-line" to obtain the 55% ACN.

To test the 55% ACN as a possible mobile phase, the "old" standard, which had been exposed to room light and temperature for several weeks was diluted 220 mg/100 mL×50/1000 to obtain a concentration of 11.0 mg/100 mL. This potentially decomposed solution was injected to find only tiny decomposition peaks in the 2.0 minute retention time region.

These peaks are not seen in the freshly prepared standard or in any of the assay solutions.

TABLE 8

Assay of the BPN-11 Samples:

| S4 | mg/100 mL | vol | DF | mg |
|---|---|---|---|---|
| 1 | 3.600 | 10 | 1 | 0.360 |
| 2 | 3.659 | 10 | 1 | 0.366 |
| 3 | 3.520 | 10 | 1 | 0.352 |
| Product | 3.790 | 60 | 10 | 22.740 |

Nanoparticles Experiments, BPN-15, BPN-16, BPN-17:

Three nanoparticles experiments, BPN-15, BPN-16 and BPN-17, were conducted on amino-flavone under the same conditions that were utilized in experiment BPN-05. The experiments were conducted on the modified Supercritical, critical or near critical fluid™ nanoparticles apparatus (FIG. 8). These experiments were carried out to provide a more concentrated solution or suspension of nanoparticles for the polymer nanoencapsulation experiments. The initial amount of feed materials in each experiment was ~100 milligrams. The primary differences between the experiments were the modes of collection.

In experiment BPN-15, the collection vessel was rinsed with ethanol to recover the nanoparticles. It appeared that all of the recovered nanoparticles dissolved in the ethanol used to rinse the vacuum flask and the decompression nozzle. The concentration was measured to be 0.745 mg/mL, about 50% greater than the measured solubility of aminoflavone in methanol (0.48 mg/mL). This concentration was measured by HPLC. There is a second peak eluting after the aminoflavone peak. It is unclear if this is a breakdown product or an impurity.

In experiment BPN-16, the collection vessel was rinsed with DI water to recover the nanoparticles. The DI water was not very effective in flushing the nanoparticles off the collection vessel, especially the stainless steel decompression nozzle. Based on dried weight analysis, the recovered sample weight was 19.6 mg, ~20%. By HPLC analysis, 36.45 mg was recovered in 63 mL of DI water for a concentration of 0.58 mg/mL. Note that the chromatographic purity of the aminoflavone is consistent with the original feed, i.e., there is no second peak that could have been generated by a breakdown product or impurity. It was noted that most of the particles were stuck to the decompression nozzle; this material was cleaned off by brushing with soapy water. Particle sizes were microscopically observed and cuticle measured for the samples recovered on the filter (2 to 4 µm), the supernatant (<5 µm) and the suspension (<8 µm). The particle sizes of the settled nanoparticles were measured in the Coulter N4MD to have a mean diameter of 2 µm; a photomicrograph at a 400× magnification is shown in FIG. 10.

In experiment BPN-17, the stainless steel nozzle was grounded to remove charges that may have attracted the nanoparticles in BPN-16. This strategy worked in that very few particles were deposited on the external surface of the stainless steel nozzle. The discharged aminoflavone nanoparticles were now concentrated on the sides of the vacuum flask opposite the exit ports of the decompression nozzle. These deposits were not flushable with a stream of DI water or 1% PVA solution and had to be scraped off with a stainless steel spatula. Only approx. one (1) mg of material reached the filter. When trying to collect this material, some of it disbursed, probably due to static electricity. Based on dried weight analysis, the recovered sample weight was 44.0 mg, ~44%. By HPLC analysis, 37.67 mg was recovered in 92 mL of DI water for a concentration of 0.41 mg/mL. Note that the chromatographic purity of the aminoflavone is consistent with the original feed, i.e., there is no second peak that could have been generated by a breakdown product or impurity. Particle sizes were measured with a mean diameter of 9 µm. Microscopically, post-run particle size shapes were regular, square or round, mostly from 1 to 3 µm with a few in the 7-8 µm range (FIG. 11).

The results of BPN-15, BPN-16 and BPN-17 are summarized in Table 9.

TABLE 9

Nanoparticles Experiments (BPN-15, BPN-16, BPN-17)

| Exp. No. | Sample | Before | After |
|---|---|---|---|
| BPN-15 | Amino-flavone Drug | Irregular crystal shapes, rectangular, needle, and shafts. 25 µm to 150 µm, a few up to 700 µm | 1-3 µm (uniform), (flat square/rectangular shape) |
| BPN-16 | Amino-flavone Drug | Irregular crystal shapes, rectangular, needle, and shafts. 25 µm to 150 µm, a few up to 700 µm | Filter - Shapes are regular, square/round, 2 to 4 µm & clumpy. Supernatant - Large # of small clumps. Crystals <5 µm Suspension - Less # of smaller clumps. Crystals <8 µm |
| BPN-17 | Amino-flavone Drug | Irregular crystal shapes, rectangular, needle, and shafts. 25 µm to 150 µm, a few up to 700 µm | Shapes are regular, square/round, 1 to 3 µm, a few in the 7-8 µm range |

Nanoparticles Experiment, BPN-19:

Nanoparticles experiment BPN-19 on the aminoflavone drug was conducted on identical conditions as BPN-15, BPN-16 and BPN-17. The primary difference is that the nanoparticles were collected in a 1% PVA solution to be utilized in the next polymer nanospheres experiment designed to increase the concentration of the drug relative to the polymer in the final product.

Note that in this experiment, the discharged material was evenly distributed on the outside of the nozzle and the interior of the collection flask. There was no major concentration of material on the glass vessel opposite the nozzle holes as seen in the previous run. The nozzle was removed from the flask before the flask was washed with 1% PVA. Due to the swirling action during the washing, the sample material was removed from the flask wall. The nozzle was replaced inside the flask and then subjected to the swirling action. This product recovery method worked quite well. Approximately 4.2 mg of material was recovered from the filter. Note that the vacuum pump was on for 45 minutes (in error) during this run instead of the nominal 30 minutes. This could have contributed to the higher recovery on the filter.

The three (3) dry weight analysis samples were air dried over night, but had to be further dried in the vacuum oven for one (1) hour at 60° C. due to the large variation in their weights. After this drying, the weights were consistent and averaged 9.4 mg, a weight that included the contribution of the PVA in the 1.0 mL sample. The average dry weight of the 1% PVA should be around 10 mg and was measured to be 9.6 mg. The dry weight analyses of the samples are thus incorrect and could not be used for determining concentration.

By HPLC analyses of two samples, 42.8 mg was recovered in 96 mL of 1% PVA for a concentration of 0.45 mg/mL. The chromatographic purity of the aminoflavone is consistent with the original feed, i.e., there is no second peak that could have been generated by a breakdown product or impurity.

The pre-run particles were irregular crystal shapes, rectangular, needles/shafts, 25×150 μm; some were up to 700 μgm. Microscopically, post-run particle size shapes were regular, square or round, mostly from 1 to 5 μm with a few in the 7-9 μm range(FIG. 12). The Coulter Particle Size Analyzer indicates that the average particle size was around 5.3 μm.

Nanoparticles Experiment, BPN-21:

BPN-21 was performed utilizing the Nanoparticle (Comminution) Apparatus, Drawing #9706-001 rev 4 on 17-allylamino demethoxygeldanamycin (17-AGG), utilizing the process conditions used in BPN-19.

After decompression, a small amount of material was concentrated on the glass vessel wall opposite the nozzle holes. It seems that the majority of the sample material stayed inside the nozzle housing, mainly on the impact element and inside the holes. The removal procedure required a lot of scraping and flushing. It may be that this material has an opposite electrical charge then the aminoflavone drug.

Figures 13A, 13B:
FIG. 13a is a photomicrograph of 17-AAG Particles before supercritical, critical or near critical fluid Particle Size Reduction (BPN-21) at a Magnification of 200×.
FIG. 13b is a photomicrograph of 17-AAG Particles after supercritical, critical or near critical fluid Particle Size Reduction (BPN-21) at a Magnification of 200×.

Microscopically, the pre-run particles were rectangular crystals with two common sizes, 19×50 μm, and 25×100 μm or less. Post-run, the particles were mostly round, majority in the 1 to 3 μm range with a few in the 5 to 10 μm range (FIG. 13a and 13b). The mean diameter of the particles measured on the Coulter N4MD was 2.7 μm, which agrees well with the microscopic observation. This value was obtained by mixing up the suspension of nanoparticles before taking a measurement. Prior to this mixing, the mean particle size of 17-AAG in the supernatant was 0.8 μm.

The total volume collected was 89 ml of 1% PVA containing the 17-AAG nanoparticles. Approximately 1.8 mg of material was recovered from the filter. The three (3) dry weight analysis samples (1.0 mL each) were air dried over the weekend. Their weights were consistent but still high, probably due to the PVA content. Their average weight was 10.9 mg. By difference, the average weight of the dried 17-AAG was 1.3 mg giving a concentration of 1.3 mg/mL and a recovered quantity of 115.7 mg or a yield of 117% since the starting amount was 99.1 mg. By HPLC analysis, the concentration of 17-AAG was 7.67 mg/100 mL in the product and 1.174 mg/100 mL in the supernatant. HPLC analysis also indicated an aminoflavone impurity in the product that was confirmed by running a mixed standard on the HPLC.

The ratio of 17-AAG to aminoflavone to 17-AAG was 9.6 in the product (BPN-21) mixture and 17.0 in the supernatant, indicating that the aminoflavone was preferentially suspended or solubilized (unlikely) in the 1% PVA solution.

4.2 Solubility Experiments

Solubility experiments were carried out on specific drug candidates in several solvent systems for operational rather than formulation strategies. Measurements were made in methanol, ethanol, water and specific SFS mixtures. The results are discussed below:

4.2.1 Preliminary Solubility Experiments in Methanol

Samples were weighed into 20-mL scintillation vials and 10 mL of methanol pipetted into each vial. Samples 2 and 4 dissolved quickly and completely; however, a small amount of solid material was seen in vials 3 and 5. An additional 10 mL of methanol was added to each of these vials. Now sample 3 dissolved completely, but particles still remained in sample 5. An additional 20 mL of methanol was added to sample 5, but on sonication, the small quantity of particles still remained. The preliminary solubility data are listed in Table 10.

TABLE 10

Preliminary Solubility of Certain Anticancer Compounds in Methanol

| Sample # | mg/10 mL | Volume (mL) | S = mg/100 mL |
|---|---|---|---|
| 2 | 16.3 | 10 | >163 |
| 3 | 17.4 | 20 | >87 |
| 4 | 22.0 | 10 | >220 |
| 5 | 19.3 | 40 | 48 |

4.2.2 Solubility of Aminoflavone in DI Water and 1% PVA

Procedure:
1. Weigh 5-10 mg of Aminoflavone into two 20 mL scintillation vials.
2. Pipette 10 mL of water into Vial A and 10 mL of 1% PVA into Vial B.
3. Shake the vials gently for about 5 minutes. Then let stand for 30 minutes.
4. Carefully withdraw 0.9 mL from each vial for HPLC Analysis
5. Shake the samples again and transfer to 50 mL Centrifuge tubes.
6. Centrifuge for 20 minutes at 2500 rpm
7. Again carefully withdraw 0.9 mL from each for HPLC Analysis.

The results are listed in Tables 11 and plotted in FIG. 14. The average solubility of aminoflavone in DI water and 1% PVA after mixing vigorously but before centrifugation was 10.68 and 12.05 μg/mL respectively. After centrifugation, the average solubility of aminoflavone in DI water and 1% PVA was respectively, 0.33 and 0.22 μg/mL.

Shaking the Aminoflavone in either water or 1% Aqueous PVA results in a dispersion of small particles that are difficult to see. They are suspended in the solution. HPLC duplication will be very poor since the "solution" is not uniform suspension of different size particles. Centrifugation will settle most of these particles to results in a significantly lower assay value.

TABLE 11

Solubility of Aminoflavone in DI Water and 1% PVA

|  | mg/100 mL | mg/mL | μg/mL | μg/mL |
|---|---|---|---|---|
| Wat-1 | 0.784 | 0.00784 | 7.84 | 10.68 |
| Wat-2 | 1.012 | 0.01012 | 10.12 |  |
| Wat-3 | 1.408 | 0.01408 | 14.08 |  |
| PVA-1 | 1.398 | 0.01398 | 13.98 | 12.05 |
| PVA-2 | 1.011 | 0.01011 | 10.11 |  |
| WatC-1 | 0.034 | 0.00034 | 0.34 | 0.31 |
| WatC-2 | 0.027 | 0.00027 | 0.27 |  |
| PVAC-1 | 0.020 | 0.00020 | 0.20 | 0.22 |
| PVAC-2 | 0.023 | 0.00023 | 0.23 |  |

Wat - DI water;
PVA - 1% PVA;
WatC - DI water after centrifugation;
PVAC - 1% PVA after centrifugation 4.2.3 Solubility of S4 (17-AAG) and S5 (Aminoflavone) in Methanol and Ethanol Application: S4 and S5 Standards
HPLC Method
Column: Phenomenex Luna C18(2), 15-cm×4.6 mm.
Buffer Concentrate (BC): 100 mL Et$_3$N×80 mL 85% H$_3$PO$_4$ to 1000 mL with water.
Mobile Phase B=250 mL ACN+10 mL of BC to 1000 mL with water.
Mobile Phase C=100% ACN Isocratic Mixture: 60% Phase B and 40% Phase C.
Alternatively, use 55% Acetonitrile with 3-mL Buffer Concentrate/1000 mL
Flow=1.5 mL/min Temperature=30° C. Wavelength=330 nm
Injection=20 µL
Preparation of the Mixed Standard
Stock S5=4.363 mg/100 mL in Methanol
Stock S4=10.00 mg/100 mL in Methanol
Pipette 10 mL of S5 stock into a 25 mL volumetric flask. Bring to 25 mL with the S4 stock solution. C(S5)=1.745 mg/100 mL and C(S4)=6.00 mg/100 mL. This mixed standard was used to calibrate the HPLC.

The two standards can be easily distinguished by their spectral scans. The contour plot also gives a characteristic profile for each standard.

Procedure for Formation of a Saturated Solution
1. Weigh in duplicate approximately 100 milligrams of each standard into 1.5 mL mini-centrifuge tubes.
2. Add 1.00 mL of Methanol to a S4 tube and 1.00 mL of Ethanol to the other S4 tube. Add 1.00 mL of Methanol to a S5 tube and 1.00 mL of Ethanol to the other S5 tube.
3. Shake all four tubes for 5 minutes at room temperature (25° C.).
4. Centrifuge at 6000 rpm for 10 minutes. The supernatant should be a saturated solution.
5. Assay the supernatants by HPLC. Use a 20/1000 dilution in methanol. The target absorbance is 0.40 AU. A reasonable absorbance range is 0.10 to 1.20. If the absorbance that is found is outside of this range, dilute appropriately to bring the absorbance close to 0.40.

Solubility Results:
The measured solubilities of aminoflavone and 17-AAG in methanol and ethanol at 25° C. are listed in Table 12.

TABLE 12

Solubilities of Aminoflavone and 17-AAG in Methanol and Ethanol at 25° C.

|  | mg/100 mL | DF | Solubility (mg/100 mL) | Solubility (mg/mL) |
| --- | --- | --- | --- | --- |
| S5 in Methanol | 5.597 | 50 | 280 | 0.280 |
| S5 in Ethanol | 4.807 | 50 | 240 | 0.240 |
| S4 in Methanol | 21.302 | 200 | 4260 | 4.260 |
| S4 in Ethanol | 7.392 | 200 | 1478 | 1.478 |

4.2.4 Supercritical, Critical or Near Critical Fluid™ Solubility Experiments

In a typical run, polymer was packed into the sample vessel, layer by layer, interspersed with glass wool in order to maximize the contact area between the supercritical fluid and the polymer, and minimize mass transfer resistance. The temperature of the system was adjusted to a desired level via an external temperature control unit (not shown in the diagram).

Syringe pumps A and B were charged with carbon dioxide and ethanol as cosolvent, respectively, and brought to operating pressure via a computerized controller. The controller was used to set the volume ratio of supercritical carbon dioxide and ethanol. The supercritical, critical or near critical fluid mixture was then charged to the system. When the pressure reached the desired level, the circulation pump was turned on to ensure that the supercritical, critical or near critical fluid and polymer were thoroughly mixed. After the desired mixing time was achieved, the 6-port injection valve was then switched to the "sampling" position to trap the polymer dissolved in the supercritical, critical or near critical fluid stream. The supercritical, critical or near critical fluid and polymer in the sample loop was then discharged into a sample collection vessel. A suitable solvent, such as methanol or acetone, was then used to flush the polymer from the sample loop, and nitrogen gas used to displace all fluids from the sample loop. The collected sample was then analyzed to determine the amount of polymer solubilized in the sample loop of known volume.

Solubility Experiments BPN-06, BPN-07 and BPN-08

Three supercritical, critical or near critical fluid solubility experiments were conducted on the aminoflavone prodrug (NSC 686288). The experiments were conducted with 100% (neat) Freon-22 at 3,000 psig (BPN-06), and 40° C., 90% Freon-22/10% ethanol at 3,000 psig and 40° C. (BPN-07) and 80% Freon-22/20% ethanol at 3,000 psig and 40° C. (BPN-08). These supercritical, critical or near critical fluid and conditions were selected on the basis of previous experience.

A 5.0 mL sample loop was utilized and each collection vial contained 5.0 ml of the same liquid as the sample loop rinse. Methanol was used as the collection fluid and sample rinse in BPN-06; ethanol was utilized as the collection fluid and sample rinse in BPN-07 and BPN-08. Samples were collected after circulation for 60, 75, 90, 105 and 120 minutes; the sample loop was then flushed of CO2 (except BPN-06). The fractions were then analyzed by HPLC. The results of this investigation are present in Table 13. Each solubility data point is the average of 5 measurements.

TABLE 13

Solubility of Aminoflavone in Supercritical, critical or near critical fluid ™ Freon-22 and Ethanol at 3,000 psig and 40° C.

| Exp. No. | Freon-22 (vol %) | Ethanol (vol %) | Solubility (mg/ml) |
| --- | --- | --- | --- |
| BPN-06 | 100 | 0 | 0.065 |
| BPN-07 | 90 | 10 | 0.108 |
| BPN-08 | 80 | 20 | 0.116 |

The solubilities were much lower than anticipated, diminishing the possibility of a one-step polymer nanoencapsulation process for aminoflavone.

4.3 Polymer Nanospheres Experiments

Two polymer nanospheres experiments were conducted with biodegradable PLGA polymers and surrogate compounds, in order to evaluate the protocols and supercritical, critical or near critical fluid Nanosphere Apparatus (FIG. 3). The experiments were as follows:

BPN-03 material—10 mg Surrogate Compound 1 and 460 mg Resomer RG-502 Polymer
BPN-04 material—33.7 mg Surrogate Compound 1 and 100.2 mg Resomer RG-502 Polymer There are several different ways that the supercritical, critical or near critical fluid Nanospheres experiments can be conducted. In these runs the surrogate compound and the PLGA were each weighed out, mixed and placed in the solids chamber in the high-pressure circulation loop. We wanted to test the concept of solubilizing both the surrogate compound and the PLGA in Supercritical, critical or near critical fluid, and then decompressing the mixture into a collection fluid containing 1% PVA. By taking this approach, we could avoid the need for making nanoparticles and simply the process from a two-step one to a single-step process.

For these experiments, the solubilities of both the PLGA and surrogate compound are important to define process conditions. We utilized the solubilities of these compounds in supercritical, critical or near critical fluid from previous research (data not shown) to define run conditions:
   Supercritical, critical or near critical fluid—Freon-22
   System Pressure—3,000 psig
   System Temperature—40° C.
   Collection Fluid—100 ml of 1% PVA (added to depressurization chamber)
   System Flow Rate—1.0 ml/min
   Circulation Time—Sixty (60) minutes
   Collection Time—Sixty (60) minutes After the circulation cycle was completed in the high pressure loop, the SFS pump was placed in the constant flow mode, the discharge valves were opened and the collection phase started. The samples were then analyzed for surrogate compound 1 content by HPLC analysis.

The results from these experiments are still being evaluated. Based on the preliminary evaluation, some minor adjustments are required to the equipment configuration and operating procedure.

Figure 16:
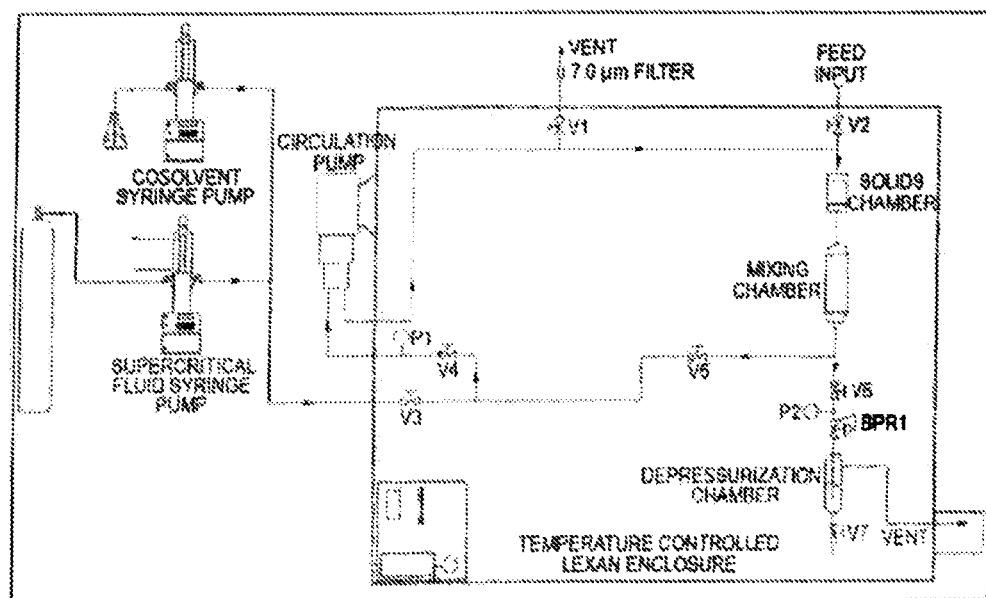
FIG. 16 depicts a Modified Supercritical, critical or near critical fluid Polymer Nanospheres Apparatus.

Polymer Nanospheres Experiment BPN-12:

The polymer nanospheres equipment (FIG. 3) was modified as shown in FIG. 16 to conduct the polymer nanospheres experiment BPN-12 to encapsulate in aminoflavone. In this modification, the static in-line mixture is removed and the circulation is maintained in a clockwise manner.

The strategy in this experiment was to feed aminoflavone into the system in solution form, and utilize this solvent mixture as the cosolvent for dissolving the PLGA polymer in the solids chamber. After mixing these solutes in the high-pressure circulation loop, the Supercritical, critical or near critical fluid mixture is decompressed via the valve V6 into PVA solution in the depressurization chamber.

The experimental design was based on the solubility of PLGA in 90% $CO_2$::10% ethanol. At 3,000 psig and 45° C., PLGA has a solubility of approximately 4 wt % (~0.04 mg/ml) in 90% $CO_2$::10% ethanol. Thus, 250 mg Resomer RG-502 was placed in the solid chamber (two layers of polymer within three layers of cotton). A 100 ml ethanol solution was made containing 0.5 mg/ml aminoflavone and the pump was charged with 95 ml of the cosolvent; 5 ml was retained for HPLC analysis. Note: The aminoflavone used were the nanoparticles generated in experiment BPN-05. The flow rate was designed to be 2.2 ml min (2.0 ml/min $CO_2$ and 0.2 ml/min ethanol containing aminoflavone). A run time of 120 minutes was designed to provide sufficient Supercritical, critical or near critical fluid™ volume (264 ml) to dissolve the 100 mg PLGA and provide 12 mg aminoflavone.

After loading the solids chamber, the high-pressure circulation loop is first pressurized to 1,000 psig with $CO_2$. 16 ml of ethanol is then injected into the 160-ml pressurized circulation loop, which is then pressurized up to 3,000 psig with $CO_2$. The Supercritical, critical or near critical fluid™ mixture is maintained at 45° C. by a space heater within the apparatus. The mixture is circulated in the high-pressure loop for 60 minutes with the gear pump running at half speed to allow the PLGA to equilibrate with the Supercritical, critical or near critical fluid mixture.

After 60 minutes, valves V5 and V6 were simultaneously opened allowing 2.2 ml/min of the Supercritical, critical or near critical fluid to flow into the circulation loop and 2.2 ml minute to exit through the back pressure regulator through a 0.069" nozzle into the depressurization chamber containing 100 ml 1% PVA.

While setting the back-pressure regulator, some PVA was lost due to aggressive discharge. Forty (40) minutes into the collection process, V5 was closed thus eliminating the circulation loop. The run terminated for the day, sample collected from the depressurization chamber. On the following day, the depressurization chamber reloaded with 100 ml of PVA. The second collection process ran for approx. 4.5 hours. The system was then flushed with $CO_2$ for approximately 80 minutes.

TABLE 14

Summary of Different BPN-12 Fractions

| BPN-12 Samples | Particle Size Observations (Microscope) | Weight Mean Size Coulter (µm) | Volume (ml) | Amino-flavone (mg) |
|---|---|---|---|---|
| First Collection | Some slivers 4 × 20 µm, a few squares 10 µm, and some round 2 µm | 1.3 | 31 | 2.93 |
| Second Collection | Shafts 1 × 15 µm and less | 3.0 | 87 | 24.95 |
| CO2 Flush | Shafts 3 × 25 µm and less | 1.9 | 2 | 0.88 |
| Overflow* | A few shafts 1 × 10 µm and less | 3.0 | 42* | 0.98 |
| Wash | Shafts 1 × 10 µm and less | 0.35 | 500 | 21.57 |

*Overflow from the first collection

Post run analysis of the contents of the solids chamber had decreased by 26.7 milligrams PLGA. Based on the Supercritical, critical or near critical fluid™ volume (315 minutes× 2.2 ml/min=693 ml) and the projected 4 wt % solubility, the amount of PLGA utilized should have been 27.72 milligrams PLGA.

The amount of aminoflavone utilized should have been 47.5 mg; based on Table 14, the amount recovered was actually 51.31 mg. The ratio of polymer:drug was approximately 0.5:1.

Sample Analysis:
The sample was from BPN-12, $2^{nd}$ collection. Previously, 2.00 mL had been removed for analysis. Now 85 mL remained for analysis.

Procedure:
1. Determine the tare weight of a 47 mm 0.45 micron Nylon 66 filter disc.
   Result: 60.8 mg
2. Filter the entire sample through the filter disc.
   Result: After about 25 mL, the filtration rate slows considerably. Thereafter, the flow is slow, but steady. The total filtration time was about 30 minutes. The filter disc contained all the yellow particles. The particles could not be scrapped from the disc. The filtrate contained no visible color.
3. Place the yellow filter disc in the vacuum oven for 2 hours at room temperature.
   Result: The increase in weight of the yellow disc was 26.7 milligrams
   Note: More data is needed on the errors that may occur in this procedure. Initially, three discs should have been extracted with 100% methanol to determine the variability of the tare weights and to see if there are extractables in the discs. Then, after the disc was extracted to remove the Aminoflavone and Resomer, it should have been weighed to determine if insoluble matter had been included in the weight.
4. Extract the disc with Methanol and bring to 100 mL with methanol.
   Result: Nearly all of the color was extracted with about 60 mL of methanol. Then additional methanol was added to make the extraction quantitative and to bring the total volume to 200 mL in a 200 mL volumetric flask. The calculated concentration was then 26.7 mg/200 mL or 13.35 mg/100 mL.

5. Assay the methanol extract for Aminoflavone.

Result: The HPLC scan showed a single peak at 4.331 minutes with a very slight solvent front disturbance. The contour plot indicated weak absorbance out to 500 nm—and suggested the presence of a low level of Resomer; however, this low level is likely due to Resomer on the surface of Aminoflavone particles.

The 13.35 mg/100 mL solution assayed at 7.430 mg aminoflavone/100 mL. Therefore, the solids extracted contained 100×7.430/13.35 or 55% aminoflavone. This indicates that the polymer nanospheres had a polymer:drug ratio of 1.2:1.0.

Conclusions:
1. The level of material in the solvent front of the filtrate is significantly higher than the level of solvent front material in the methanol extract of the yellow filter disc.
2. The filter disc method should not be used. It is too difficult to get a small quantity of particulate from the disc to obtain a weight of the solid. Instead, the suspension should be centrifuged and the precipitate washed with a small quantity cold water.
3. The solubility of Aminoflavone, PVA, and Resomer should be determined in water.
4. An analytical method should be developed for Resomer and PVA. This would not be possible with UV detection if the Resomer and PVA were true to their theoretical molecular formulas. However, they are not—and contain sufficient unsaturation so that UV detection is a possibility. A starting point for method development could be the original HPLC gradient method in which the starting solvent is 100% water and not isocratic 60% ACNB. Previously, the aminoflavone was run in this system to obtain the following:

Both Resomer and PVA should be run in this system to see if a usable HPLC method can be developed for these components.

Figure 17:
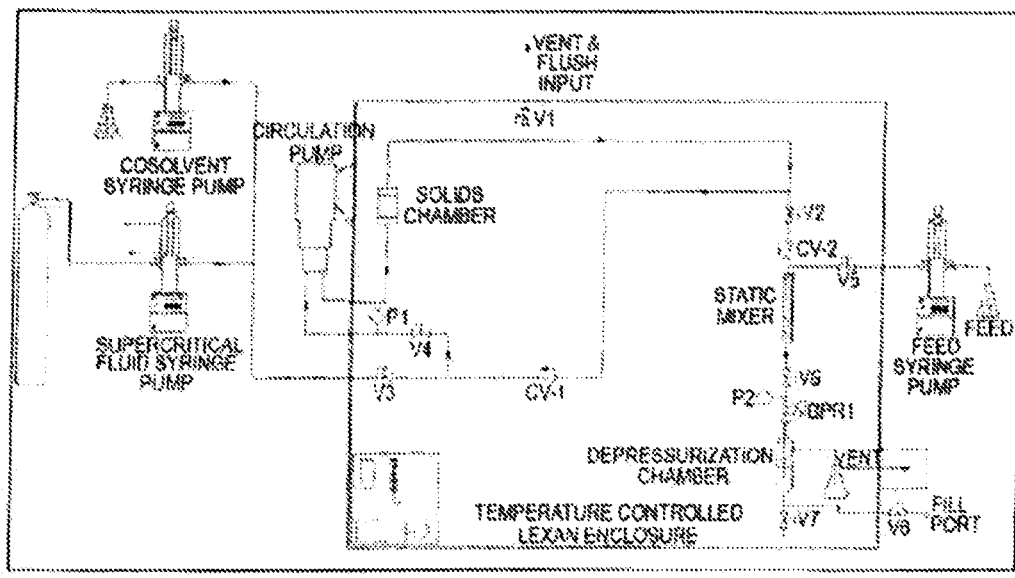
FIG. 17 depicts a Supercritical, critical or near critical fluid Polymer Nanospheres Apparatus (Second Modification)

Polymer Nanospheres Experiment BPN-13:

After run BPN-12, the Supercritical, critical or near critical fluid™ polymer nanospheres apparatus was modified by the re-installation of the static inline mixer downstream of the high-pressure circulation loop (FIG. 17). This modification allows the introduction of a drug solution or drug nanoparticles stream downstream of the high pressure circulation loop but upstream of an in-line mixer to allow thorough mixing between the polymer-rich Supercritical, critical or near critical fluid™ stream and the drug-rich stream. A third pump was added to introduce the drug-rich stream. These modifications were done so that the different Supercritical, critical or near critical fluid™ could be tested in view of the limited solubilities of polymer in the $CO_2$:cosolvent mixture and of the aminoflavone in the cosolvent in experiment BPN-12.

For this experiment, Freon-23 was selected for testing since PLGA had a solubility of 0.20 mg/mL in Freon-23 at 3,000 psig and 30C versus ~0.04 mg/ml in 90% $CO_2$::10% ethanol (conditions utilized in BPN-12). At a flowrate of 2.0 mL/min, around 0.4 mg/min PLGA will be consumed. To achieve a 10:1 ratio, aminoflavone concentration will have to be 0.04 mg/min requiring a concentration of 0.2 mg/mL for a flowrate of 0.2 mL/min. For a run time of 100 minutes, 40 mg of PLGA and 4 mg of aminoflavone.

Assuming 25% overage for transient losses during start-up and shutdown as well as for dead volumes in the system, 50 mg of PLGA was loaded in the solids chamber and a solution of 5 mg of aminoflavone in 25 mL of ethanol was prepared.

After loading the polymer in the solids chamber and pressuring the high-pressure circulation loop to 3,000 psig with the pump operating in the constant pressure mode and setting the backpressure regulator to operate at 3,000 psig, the fluid stream was circulated for 5 minutes with valves V3 and V2 closed. In the second step in the operational sequence, valves V2 and V3 are opened, and Freon-23 was pumped at a rate of 2.0 mL/min and the feed (drug solution) at 0.2 mL/min with V5 and V6 open for 125 minutes. The polymer-rich Freon-23 stream and the drug feed are routed through the inline static mixture and the backpressure regulator into the decompression chamber containing 1% PVA solution. At the end of the 125 minutes, with V6 closed and by opening V7, the product is collected from the depressurization chamber. The depressurization chamber is then re-filled with 100 mL of 1% PVA via valve V8. The high pressure lop is then depressurized into the PVA solution in the decompression chamber. After the decompression chamber is drained, the system was washed with 500 mL ethanol.

The different fractions including the cotton were analyzed. The results are summarized in Table 15.

TABLE 15

Summary of Different BPN-13 Fractions

| BPN-13 Fractions | Particle Size Observations (Microscope) | Mean Size Coulter (μm) | Volume (mL) | Aminoflavone (mg) |
|---|---|---|---|---|
| Product | Mostly round with some very small slivers, 1.0 to 2.0 μm | 2.8 | 38 | 4.51 |
| Overflow | N.A. | 0.8 | 71 | 0.03 |
| Depressurization | N.A. | 0.5 | 99 | 0.09 |
| Cotton | N.A. | N.A. | 20 | 0.03 |
| Wash | N.A. | 0.5 | 500 | 2.97 |

N.A. - not applicable

The product was microscopically observed to be mostly round (1.0 to 2.0 μm) with some very small slivers, measured to have a mean diameter of 2.8 μm by the Coulter N4MD particle size analyzer, and analyzed by HPLC to contain 4.51 mg aminoflavone (90% of the aminoflavone feed. A photomicrograph of BPN-13 product is shown at a magnification of 400× in FIG. 18.

By weight difference, the PLGA utilized in this experiment was 12.4 mg. Assuming all the utilized polymer contributed to the polymer nanospheres, the polymer:drug ratio was approximately 2.8:1.0.

Polymer Nanospheres Experiment BPN-14:

In order to increase the polymer drug ratio and to shorten run time, an experimental run was designed and conducted with Freon-22 in which the Resomer PLGA polymer has a higher solubility than Freon-23. At 3,000 psig and 30° C., the solubility of PLGA in Freon-22 is 9.84 mg/mL, about 50 times that of its solubility in Freon-23 at identical conditions of temperature and pressure.

The Resomer RG-502 PLGA solubilized in supercritical, critical or near critical fluid Freon-22 at 3,000 psig and 30° C. will be 19.68 mg/min at a flowrate of 2.0 mL/min. For a run time of 10 minutes, the amounts consumed would be ~200 mg. With a feed aminoflavone concentration of 0.2 mg/mL and a flowrate of 0.2 mL/min, the amount utilized will be 0.04 mg/min or 0.4 mg in 10 minutes. This combination should yield a polymer:drug ratio of 200:0.4 or 500:1.0.

A total of 207 mg of PLGA was loaded in the solids chamber and 2 mL of 0.2 mg/mL aminoflavone in ethanol was loaded in the feed pump. The experiment was conduced in the same manner as BPN-13 except the second step was conducted for only 10 minutes instead of 125 minutes. The different fractions including the cotton were analyzed by HPLC. The results are summarized in Table 16.

TABLE 16

Summary of Different BPN-14 Fractions

| BPN-14 Fractions | Particle Size Observations (Microscope) | Mean Size Coulter (μm) | Volume (mL) | Aminoflavone (mg) |
|---|---|---|---|---|
| Product | Majority are round 2.0 to 5.0 μm, some 10.0 to 15.0 μm | 0.5 | 70 | 0.043 |
| Overflow | N.A. | 0.5 | 61 | 0.019 |
| Depressurization | N.A. | 0.7 | 64 | 0.042 |
| Wash | N.A. | 0.3 | 510 | 1.387 |

N.A. - not applicable

A photomicrograph of BPN-14 product is shown at a magnification of 400× in FIG. 19.

By weight difference, the PLGA utilized in this experiment was 206.7 mg. Assuming all the utilized polymer contributed to the polymer nanospheres, the polymer:drug ratio was approximately 4,800:1.0. The likely reason that the drug did not get into the polymer-rich stream is the dead volume from the pump to the static in-line mixer; this dead volume is estimated to be around a few milliliters.

Polymer Nanospheres Experiment BPN-18:

In order to reduce the polymer drug ratio or increase the drug content over that achieved in experiment BPN-14, we elected to utilize a concentrated nanoparticles feed in this experiment.

In order to execute this strategy, several aminoflavone nanoparticles experiments (BPN-15, BPN-16 and BPN-17) were conducted. These experiments are presented and discussed in Section 5.1. The slurry from BPN-17 was centrifuged at 4,000 rpm for 30 minutes at 5° C. Most of the supernatant was removed to leave a concentrated slurry of approximately 50 mg in about 10 mL of DI water giving a concentration of about 5 mg/ML about 20 times the concentration in the feed for BPN-14.

BPN-18 was then conducted in similar fashion to BPN-14 utilizing the supercritical, critical or near critical fluid Nanospheres Apparatus 9801-01 Rev 9, in the down flow mode (FIG. 17).

Run Parameters:
Critical Fluid—Freon-22
Feed—Approx. 9.0 ml of concentrated BPN-17 Wash
System Pressure—3000 psig
System Temperature=30° C.
Polymer—Resomer RG502 (200 mg)
Collection Fluid—100 ml of 1% PVA
Critical Fluid Flow-rate—2.0 ml/min
Feed Flow-rate—0.6 ml/min
Circulation Time—Five (5) minutes
Collection Time—Ten (10) minutes
Weights:
Polymer—199.8 mg
Cotton—384.2 mg General Instructions:
Place two (2) layers of polymer between three (3) layers of cotton
Load the 1% PVA into the depressurization chamber
Run the circulation pump at ½ speed
After the circulation period is complete, set the pumps to their appropriate flow-rates
Collection Volumes:
Product—69.0 ml
Depressurization—24.0 ml
Overflow—100.0 ml
Feed Pump Wash—250.0 ml
System Wash—500.0 ml
Post Run Weights:
Polymer/Cotton—388.6 mg
Spent Polymer—195.4 mg The collected solutions, product, depressurization and overflow, were centrifuged in preparation for further assays—$1^{st}$ setting—5° C., 4,000 rpm for 30 minutes; $2^{nd}$ setting—5° C., 12,000 rpm, for 30 minutes.

The different fractions including the cotton were analyzed by HPLC. The results are summarized in Table 17.

TABLE 17

Summary of Different BPN-18 Fractions

| BPN-18 Fractions | Particle Size Observations (Microscope) | Mean Size Coulter (μm) | Volume (mL) | Aminoflavone (mg) |
|---|---|---|---|---|
| BPN-17 Supernatant | N.M. | | 84 | 0.172 |
| Feed (BPN-17 Wash) | Shapes are regular, square/round, 1 to 3 μm, a few in the 7-8 μm range | 9.08 | 6 | 20.574* |
| Product | N.M. | 0.53 | 69 | 0.0 |
| Overflow | N.M. | 0.85 | 100 | 0.0 |
| Depressurization | N.M. | 0.78 | 24 | 0.0 |
| Feed Pump Wash | N.M. | N.A. | 250 | 9.920 |
| System Wash | N.M. | N.A. | 500 | 7.690 |

*Based on a concentration of 3.429 mg/mL
N.M. - not measured

The HPLC analysis of the BPN-18 product indicates that no aminoflavone was incorporated in the polymer nanospheres. A photomicrograph is shown at a magnification of 400× in FIG. 20. The likely reason that the drug did not get into the polymer-rich stream is that the nanoparticles remained in the pump and the system, as indicated by aminoflavone in the feed pump wash and the system wash. The positive displacement pump was ineffective in introducing the slurry suspension into the polymer nanospheres apparatus. A positive displacement slurry pump may be more efficient in introducing the slurry into the system. Another possible reason is the particle size distribution with particles up to 7-9 μm may have caused plugging in the distribution lines. This possibility could be eliminated since high backpressures were not observed during the run.

Polymer Nanospheres Experiment BPN-20:

To avert some of the nanoparticles pumping difficulties in BPN-18, the aminoflavone nanoparticles in 1% PVA solution collected from BPN-19 was placed in the decompression or product formation chamber of the Supercritical, critical or near critical fluid™ Polymer Nanospheres apparatus 9801-

01, Rev. 9 (FIG. 17) in polymer nanospheres experiment No. BPN-20.

Run Parameters:

| | BPN-20 |
|---|---|
| Critical Fluid | Freon-22 |
| Feed | NA |
| System Pressure | 3000 psig |
| System Temperature | 30° C. |
| Polymer | 200 mg (RG-502) |
| Collection Fluid | 86 ml (BPN-19 Product) |
| Critical Fluid Flow rate | 1.0 ml/min |
| Feed Flow rate | NA |
| Circulation Time | Five (5) minutes |
| Collection Time | Twenty (20) minutes |
| Material | Aminoflavone Drug |
| Polymer Weight | 201.8 mg |
| Cotton Weight | 326.5 mg |

Collection Volumes:

| | |
|---|---|
| Product | 55.0 ml |
| Depressurization | 57.0 ml |
| Overflow | 38.0 ml |
| System Wash | approx. 530 ml |
| Spent Polymer Weight | 201.8 mg |

Operational Procedure:

Two layers of Polymer were placed between three layers of cotton inside the solids chamber.

The collection fluid solution was loaded into the depressurization chamber.

After system pressure is reached, the circulation pump is turned ON at ½ speed.

After the circulation time has expired, the SFS pump is set to 1.0 ml/min.

Maintain system pressure as necessary.

After the collection time has expired, collect the contents of the depressurization chamber.

Before system depressurization, add 100 ml of 1% PVA to the depressurization chamber.

After system depressurization, collect the contents of the depressurization chamber.

Flush system with approx. 500 ml of Ethanol and collect.

Note: At a 1.0 ml/min flow rate, very little, if any, overflow is being generated during the collection process.

The concentrations and amounts of aminoflavone in the BPN-20 product mixture and supernatant in 1% PVA are listed in Table 18:

TABLE 18

Amounts and Concentrations of Aminoflavone in BPN-20 Product and Supernatant

| ID | Volume (mL) | DF | HPLC Conc. (mg/100 mL) | Amount (mg) | Average Amount (mg) | Average Conc. (mg/mL) |
|---|---|---|---|---|---|---|
| BPN-20 Feed (BPN-19 Product) | 96 | 5.0 | 8.891 | 42.677 | 42.771 | 0.45 |
| BPN-20 Feed (BPN-19 Product) | 96 | 5.0 | 8.932 | 42.874 | | |
| BPN-20 Product | 82 | 5.0 | 8.919 | 36.568 | 36.693 | 0.45 |
| BPN-20 Product | 82 | 5.0 | 8.980 | 36.818 | | |
| BPN-20 Supernatant | 82 | 2.5 | 1.272 | 2.608 | 2.606 | 0.03 |
| BPN-20 Supernatant | 82 | 2.5 | 1.270 | 2.604 | | |

The average concentration in the supernatant is 30 µg/mL, about 3 times the apparent solubility of 12 µg/mL and about 15 times the actual solubility of 0.22 µg/mL in 1% PVA solution.

Figures 21A, 21B:
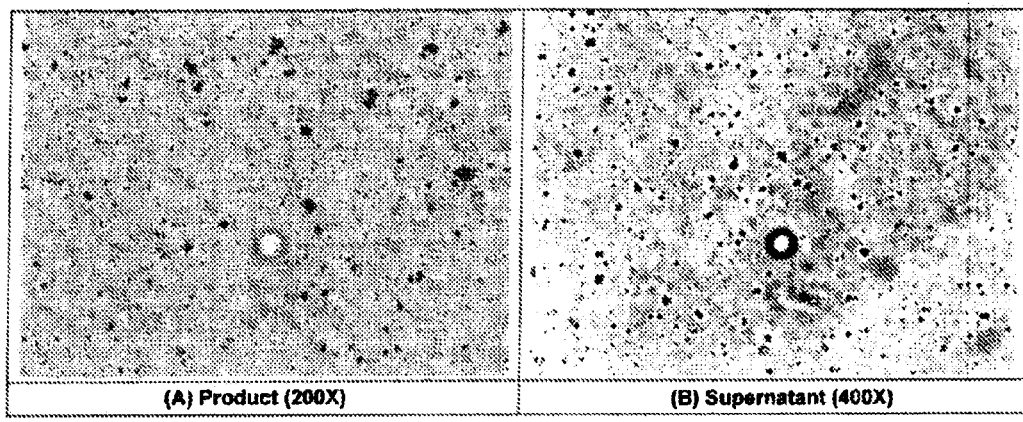
FIG. 21a is a photomicrograph of BPN-20 Polymer Nanospheres Product.
FIG. 21b is a photomicrograph of BPN-20 Polymer Nanospheres Supernatant.

Photomicrographs of the product and the supernatant are shown in FIGS. 21a and 21b.

Test for Ratio of Polymer to Aminoflavone in BPN-20 Product

Procedure:

1. Write A, B, C, and D on each of four 0.45 micron 47 mm Nylon 66 filters with a soft pencil.
2. Weigh each of the filters.
3. Draw Methanol through Filter A and set on a paper towel to dry.
4. Weigh about 10 mg of aminoflavone onto Filter B and get an accurate weight.
5. Draw 100 mL of Methanol through Filter B and bring to 100 mL in a 100 mL vol flask
6. Set Filter B aside to dry on a paper towel.
7. Draw 20 mL of 1% PVA through Filter C and set on a paper towel to dry.
    Save the Filtrate for HPLC Assay
8. Draw 20 mL of BPN-20 yellow ppt through Filter D and set on a paper towel to dry.
    Save the Filtrate for HPLC Assay
9. Place all four filters in the vacuum oven for 1 hour at 60 C. Then weigh the filters.
10. Draw 100 mL of Methanol through Filters C and D. Bring to 100 mL with Methanol.
11. Dry, vacuum oven, and get an accurate weight on filters C and D.

Results:

A. Obtain a tare weight for a filter disc. Wash it with methanol. Dry in vacuum oven.
    Initial weight=68.4 mg
    Final weight=68.4 mg
    Result: The filter disc does not change its weight after washing and drying.
B. 9.9 mg Aminoflavone weighed onto Disc B and washed off with methanol.
    Initial weight=68.0 mg
    Final Weight=68.2 mg
    Result: The mass increase is 0.2 mg, which may not be significant.
C. 1% PVA passed through Filter C and was then vacuum dried.
    Initial weight=67.7 mg
    Final Weight=70.6 mg
    Result: The increase in weight is 2.9 milligrams—which is significant.

D. 20 mL of material from the bottom of BPN-20 was passed through the filter

The material was then placed in the vacuum oven for 1 hour at room temp.

Initial Weight=67.1 mg

Final weight=79.2 mg

Result: The weight increase was 12.1 milligrams.

If 2.9 mg is contributed by PVA, then 9.2 mg is the "extra" weight.

A photograph of the filter papers is shown in FIG. 59.

HPLC Analysis of Disc D Filtrate:

The 20 mL of BPN-20 bottom yellow was passed through a 0.45 Nylon 66 filter.

All yellow remained on the filter.

The filtrate assayed at 0.030 mg/100 mL or 0.0015 mg in the 20 mL.

Thus the aminoflavone is essentially insoluble in 1% PVA and values higher than 0.002 mg/100 mL are due to suspended particles—not dissolved material.

HPLC Analysis of Disc D Methanol Extract:

The filter disc was extracted in methanol yielding 5.5 milligrams of aminoflavone by HPLC This suggests that there is 3.7 milligrams of excess is the Resomer polymer.

Thus, the ratio of polymer:drug in the BPN-20 product was 3.7:5.5 or 0.7:1.

Test for Ratio of Polymer to Aminoflavone in BPN-20 Supernatant

Four discs were tared. To discs 1, 2, and 3, 10, 20, and 40 mL of 1% PVA was passed through. To disc #4, 20 mL of BPN-20 supernatant was passed through.

All four discs were dried for 1 hour at 60 C and high vacuum before weighing.

TABLE 19

Filtered Weights of 1% PVA and BPN-20 Supernatant

| | Tare (g) | Gross (g) | Net (mg) |
|---|---|---|---|
| 1-10 mL | 0.0657 | 0.0683 | 2.6 |
| 2-20 mL | 0.0657 | 0.0683 | 2.6 |
| 3-40 mL | 0.0658 | 0.0687 | 2.9 |
| 4-BPN-20 | 0.0671 | 0.0703 | 3.2 |

Conclusions:

1. 1% PVA deposits about 2.7 milligrams of solids on the filter.

Passing a larger volume of 1% PVA through the filter increases the weight very slightly.

2. The increase in weight for BPN-20 is too small to be meaningful.

HPLC Assay of Yellow Deposit on Disc #4-BPN20

The disc was extracted with 10 mL Methanol yielding 1.415 mg/100 mL of S5.

Thus the amount of S5 in the disc was 0.14 mg

The Excess weight was 3.2-2.6=0.60 mg

Thus, the ratio of polymer:drug in the BPN-20 supernatant was 0.44:0.14 or ~3:1. This ratio is similar to that of BPN-13.

Polymer Nanospheres Experiment BPN-22:

Polymer nanospheres experiment No. BPN-22 was conducted at the same conditions with BPN-20 except with 17-AAG. The BPN-21 nanoparticles in 1% PVA was used in the collection (decompression) chamber for this experiment.

Run Parameters:

| BPN-22 | |
|---|---|
| Critical Fluid | Freon-22 |
| Feed | NA |
| System Pressure | 3000 psig |
| System Temperature | 30° C. |
| Polymer | 200 mg (RG-502) |
| Collection Fluid | 76 ml (BPN-21 Product) |
| Critical Fluid Flow rate | 1.0 ml/min |
| Feed Flow rate | NA |
| Circulation Time | Five (5) minutes |
| Collection Time | Twenty (20) minutes |
| Material | 17-Allylamino Demethoxygeldanamycin |
| Polymer Weight | 199.2 mg |
| Cotton Weight | 351.4 mg |

Collection Volumes:

| Product | 67.0 ml |
|---|---|
| Depressurization | 51.0 ml |
| Overflow | 44.0 ml |
| System Wash | approx. 530 ml |
| Spent Polymer Weight | 198.2 mg |

Process Procedure:

Two layers of Polymer were placed between three layers of cotton inside the solids chamber.

The collection fluid solution was loaded into the depressurization chamber.

After system pressure is reached, the circulation pump is turned ON at ½ speed.

After the circulation time has expired, the CF pump is set to 1.0 ml/min.

Maintain system pressure as necessary.

After the collection time has expired, collect the contents of the depressurization chamber.

Before system depressurization, add 100 ml of 1% PVA to the depressurization chamber.

After system depressurization, collect the contents of the depressurization chamber.

Flush system with approx. 500 ml of Ethanol and collect.

Note: At a 1.0 ml/min flow rate, very little, if any, overflow is being generated during the collection process.

The concentrations and amounts of 17-AAG in the BPN-22 product mixture and supernatant in 1% PVA are listed in Table 20.

TABLE 20

Amounts and Concentrations of 17-AAG in BPN-22 Product and Supernatant

| | Concentration (mg/100 mL) | | | | Amount (mg) | | Ratio |
|---|---|---|---|---|---|---|---|
| ID | S5 | S4 | Vol | DF | S5 | S4 | S4/S5 |
| BPN 21 Prod Supernatant | 0.102 | 1.735 | 20 | 1 | 0.020 | 0.347 | 17.0 |
| BPN 21 Product | 0.801 | 7.67 | 20 | 1 | 0.160 | 1.534 | 9.6 |
| BPN 22 Prod Supernatant | 0.27 | 0.999 | 67 | 5 | 0.905 | 3.347 | 3.7 |
| BPN 22 Product | 0.654 | 6.547 | 65 | 5 | 2.126 | 21.278 | 10.0 |
| BPN 22 Depress | 0.092 | 0.381 | 51 | 5 | 0.235 | 0.972 | 4.1 |
| BPN 22 Overflow | 0.069 | 0.198 | 44 | 5 | 0.152 | 0.436 | 2.9 |

The aminoflavone contamination in the BPN-22 product and supernatant streams appear to have been primarily associated with the SFS Polymer Nanospheres apparatus, probably as a carryover from BPN-20 even though there was also some contamination with the feed (BPN-21 wash (product)). The apparatus was subsequently cleaned with seven (7) rinses of ethanol and methanol. The concentration of aminoflavone in the last rinse was 0.71 μg/mL. This residual concentration suggests that the apparatus needs to be modified to eliminate dead-end pockets and clean-in-place procedures require improvement.

Polymer Nanospheres Experiment BPN-23:

In this experiment, a strategy similar to BPN-13 or BPN-14 was utilized for the polymer encapsulation of 17-AAG. In order to execute on this strategy, the solubilities of 17-AAG in ethanol and methanol were first measured (reported in Section 5.2.3). Based on the high solubility of 17-AGG in methanol, we elected to emulate BPN-14 that utilized Freon-22 in which, at 3,000 psig and 30° C., the solubility of PLGA is 9.84 mg/mL.

The Resomer RG-502 PLGA solubilized in Supercritical, critical or near critical fluid™ Freon-22 at 3,000 psig and 30° C. should be ~10 mg/min at a flowrate of 1.0 mL/min. For a run time of 50 minutes, the amounts consumed would be ~500 mg. With a feed 17-AGG concentration of 20 mg/mL and a flowrate of 0.1 mL/min, the amount utilized will be 2 mg/min or 100 mg in 50 minutes. This combination should yield a polymer:drug ratio of 500:100 or 5:1.

The design required pumping only 5 mL of concentrated 17-AGG solution, which could be problematic because of dead columns between the feed pump and the nano spheres apparatus. This dead volume was measured to be ~8.5 mL. The lines were changed out from ⅛" to 1/16", reducing the dead volume to 1.9 mL. The experimental design was then modified to pump 5 mL of 20 mg/mL 17-AGG in methanol into the nanospheres apparatus while accounting for the 1.9 mL dead volume.

A total of 499.8 mg of PLGA was loaded in the solids chamber and 6.4 mL of 20 mg/mL 17-AAG in methanol was loaded in the feed pump. The experiment was conducted in the same manner as BPN-14 except for Freon-22 and feed flowrates of 1.0 and 0.1 mL/min and a run time of 50 minutes. During the feed pressurization phase of the run, the apparent volume in the pump went to zero indicating a significant dead volume in the head of the piston pump. The run was temporarily stopped and 13.6 mL of methanol was introduced into the pump, reducing the theoretical concentration to 6.4 mg/mL in the feed pump. The different fractions were analyzed by HPLC. The results are summarized in Table 21.

TABLE 21

Summary of Different BPN-23 Fractions

| BPN-23 Fractions | Particle Size Observations (Microscope) | Mean Size Coulter (μm) | Volume (mL) | 17-AAG (mg) |
|---|---|---|---|---|
| Product & Overflow | N.A. | 0.464. | 98 | 3.177 |
| Depressurization & Overflow | N.A. | 0.7 | 101 | 3.688 |
| Wash & Excess | N.A. | N.A. | 536 | 93.387 |
| Total | | | | 100.252 |

N.A. - not applicable

Figures 22A, 22B:
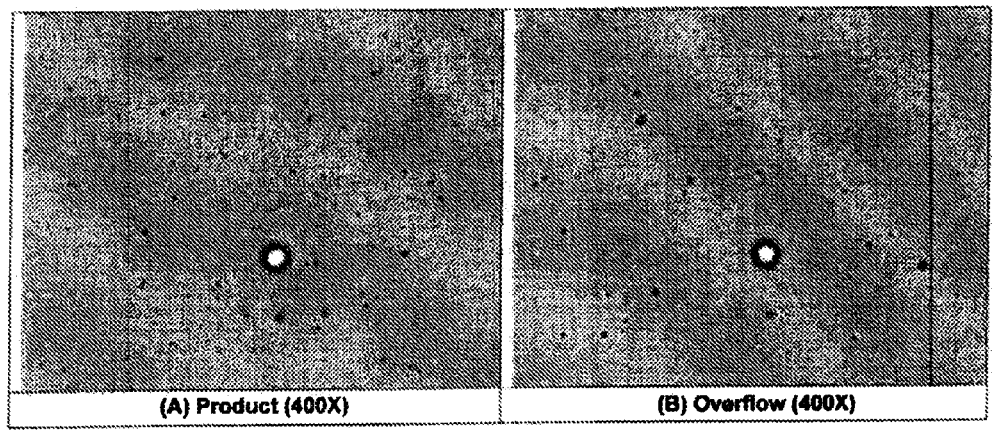
FIG. 22a is a photomicrograph of BPN-23 Polymer Nanospheres Product
FIG. 22b is a photomicrograph of BPN-23 Polymer Nanospheres Product Overflow

Photomicrographs of the BPN-23 product and overflow are shown at a magnification of 400× in FIGS. 22a and 22b.

By weight difference, the PLGA utilized in this experiment was 500 mg. Assuming all the utilized polymer contributed to the polymer nanospheres, the polymer:drug ratio was approximately 160:1. The likely reason that more drug did not get into the polymer-rich stream is phase stratification in the pump after the addition of additional methanol to compensate for dead space in the pump head.

Polymer Nanospheres Experiment BPN-24:

BPN-24 for the polymer encapsulation of aminoflavone was conducted under similar conditions as BPN-13, an experiment of reasonable quality, in order to evaluate process reproducibility.

HPLC analyses of the different fractions are summarized in Table 22 and plotted in FIG. 65.

TABLE 22

HPLC Analyses of System Washes and BPN-24 Fractions

| ID | S4 (mg/ 100 mL) | S5 (mg/ 100 mL) | Vol. (mL) | DF | 17-AAG (mg) | Amino-Flavone (mg) |
|---|---|---|---|---|---|---|
| BPN-23 2nd Wash | 0.440 | 0.014 | 600 | 1 | 2.6400 | 0.0840 |
| BPN-24 System Wash | 0.053 | 0.122 | 600 | 1 | 0.3180 | 0.7320 |
| Pump Feed Excess | 0.000 | 1.933 | 8 | 10 | 0.0000 | 1.5464 |
| Feed Pump Wash | 0.014 | 1.019 | 100 | 1 | 0.0140 | 1.0190 |
| Depress Supernatant | 0.006 | 0.100 | 10 | 1 | 0.0006 | 0.0100 |
| Overflow | 0.020 | 0.034 | 90 | 5 | 0.0900 | 0.1530 |
| Collection Overflow | 0.058 | 0.000 | 48 | 5 | 0.1392 | 0.0000 |
| Product Supernatant | 0.018 | 0.755 | 70 | 5 | 0.0630 | 2.6425 |
| Product Total | 0.027 | 1.110 | 70 | 5 | 0.0945 | 3.8850 |

Photomicrographs are shown in FIGS. 23a and 23b.

While this invention has been particularly shown and described with references to specific embodiments, it will be understood by those skilled in the art that various changes in form and details may be made therein without departing from the spirit and scope of the invention as defined by the appended claims.

The invention claimed is:

1. A method of making one or more spheres having a diameter of about 50 to 500 nanometers having a shell comprising at least one of the polymers selected from poly (D,L-lactide-coglycolide polymer) and polycaprolactone containing a poorly soluble drug selected from the group consisting of indole hydrazinecarbothioamide; fenretinide; safingol; 17-allylamino demethoxygeldanamycin and an aminoflavone drug [NSC 686288] and poorly soluble derivatives of such compounds; said method comprising the steps of forming a mixture of at least one of the polymers selected from poly (D,L-lactide-coglycolide polymer) and polycaprolactone containing a poorly soluble drug in supercritical, critical or near critical fluid selected from the compounds nitrogen, carbon dioxide, propane, nitrous oxide and fluorinated hydrocarbons, injecting said mixture in a stream in a solution comprising a cross-linking agent in a buffer to form one of more spheres having a diameter of 50 to 500 nanometers or forming a mixture of at least one of the polymers selected from poly (D,L-lactide-coglycolide polymer) and polycaprolactone in supercritical, critical or near critical fluid selected from the compounds nitrogen, carbon dioxide, propane, nitrous oxide and fluorinated hydrocarbons, injecting said mixture in a stream in a solution containing a poorly soluble drug comprising a cross-linking agent in a buffer to form one of more spheres having a diameter of 50 to 500 nanometers having a shell comprising at least one of the polymers selected from poly (D,L-lactide-coglycolide polymer) and polycaprolactone containing a poorly soluble drug.

2. The method of claim 1 wherein said one or more spheres is lyophilized.

3. The method of claim 2 wherein said poly (D,L-lactide-coglycolide polymer) is present in a ratio of 75:25 to 25:75.

4. The method of claim 2 wherein said ratio is 60:40 to 40:60.

5. The method of claim 2 wherein said ratio is about 50:50.

6. The method of claim 1 wherein said poorly soluble drug is in a buffer.

7. The method of claim 6 wherein said buffer comprises an alcohol.

8. The method of claim 7 wherein said alcohol has a concentration ranging from 1 to 50%.

9. The method of claim 8 wherein said alcohol is ethanol.

10. The method of claim 2 wherein said cross linking agent is polyvinyl alcohol.

* * * * *